(12) United States Patent
Zenz-Olson et al.

(10) Patent No.: US 12,185,979 B2
(45) Date of Patent: Jan. 7, 2025

(54) MEDICAL IMPLANT DELIVERY SYSTEM AND RELATED METHODS

(71) Applicant: ROTATION MEDICAL, INC., Plymouth, MN (US)

(72) Inventors: Nathaniel Zenz-Olson, Blaine, MN (US); Nathaniel Tran, Lakeville, MN (US)

(73) Assignee: ROTATION MEDICAL, INC., Plymouth, MN (US)

( * ) Notice: Subject to any disclaimer, the term of this patent is extended or adjusted under 35 U.S.C. 154(b) by 0 days.

(21) Appl. No.: 17/974,886

(22) Filed: Oct. 27, 2022

(65) Prior Publication Data

US 2023/0058024 A1    Feb. 23, 2023

Related U.S. Application Data

(63) Continuation of application No. 17/138,324, filed on Dec. 30, 2020, now Pat. No. 11,510,702, which is a
(Continued)

(51) Int. Cl.
*A61B 17/56* (2006.01)
*A61B 17/34* (2006.01)
(Continued)

(52) U.S. Cl.
CPC .......... *A61B 17/56* (2013.01); *A61B 17/3468* (2013.01); *A61F 2/0805* (2013.01);
(Continued)

(58) Field of Classification Search
CPC ................ A61F 2/0063; A61F 2/0805; A61F 2002/0072; A61B 17/3468; A61B 17/56; A61B 2017/564
See application file for complete search history.

(56) References Cited

U.S. PATENT DOCUMENTS

| 511,238 A | 12/1893 | Hieatzman et al. |
| 765,793 A | 7/1904 | Ruckel |

(Continued)

FOREIGN PATENT DOCUMENTS

| CA | 2390508 A1 | 5/2001 |
| CA | 2404647 A1 | 8/2002 |

(Continued)

OTHER PUBLICATIONS

Notification of Transmittal of the International Search Report and the Written Opinion of the International Searching Authority, or the Declaration for Application No. PCT/US2016/030949, 17 pages, date mailed Oct. 4, 2016.

(Continued)

*Primary Examiner* — Dinah Baria
(74) *Attorney, Agent, or Firm* — Seager, Tufte & Wickhem LLP

(57) ABSTRACT

An implant delivery device for introducing and positioning implants within patients may include a sheath member having a distal end, a proximal end, and a central longitudinal axis, the sheath member defining a lumen along the central longitudinal axis. The implant delivery device may additionally include an implant delivery shaft having a distal end and a proximal end, the implant delivery shaft disposed at least partially within the sheath member and an implant spreader assembly disposed at the distal end of the implant delivery shaft. In some embodiments, the implant delivery device may further include a cap disposed at the distal end of the sheath member, the cap obstructing at least a portion of an opening into the lumen of the sheath member.

12 Claims, 18 Drawing Sheets

Related U.S. Application Data continuation of application No. 15/147,106, filed on May 5, 2016, now Pat. No. 10,898,228.

(60) Provisional application No. 62/157,674, filed on May 6, 2015.

(51) Int. Cl.
  *A61F 2/08* (2006.01)
  *A61B 17/00* (2006.01)
  *A61B 17/02* (2006.01)
  *A61F 2/00* (2006.01)

(52) U.S. Cl.
  CPC . *A61B 2017/00473* (2013.01); *A61B 17/0218* (2013.01); *A61B 2017/3454* (2013.01); *A61B 2017/564* (2013.01); *A61F 2/0063* (2013.01); *A61F 2002/0072* (2013.01)

(56) References Cited

U.S. PATENT DOCUMENTS

| | | |
|---|---|---|
| 1,728,316 A | 9/1929 | Von Wachenfeldt |
| 1,855,546 A | 4/1932 | File |
| 1,868,100 A | 7/1932 | Goodstein |
| 1,910,688 A | 5/1933 | Goodstein |
| 1,940,351 A | 12/1933 | Howard |
| 2,034,785 A | 3/1936 | Wappler |
| 2,075,508 A | 3/1937 | Davidson |
| 2,131,321 A | 9/1938 | Hart |
| 2,154,688 A | 4/1939 | Matthews et al. |
| 2,158,242 A | 5/1939 | Maynard |
| 2,199,025 A | 4/1940 | Conn |
| 2,201,610 A | 5/1940 | Dawson, Jr. |
| 2,254,620 A | 9/1941 | Miller |
| 2,277,931 A | 3/1942 | Moe |
| 2,283,814 A | 5/1942 | La Place |
| 2,316,297 A | 4/1943 | Southerland et al. |
| 2,421,193 A | 5/1947 | Gardner |
| 2,571,813 A | 10/1951 | Austin |
| 2,630,316 A | 3/1953 | Foster |
| 2,684,070 A | 7/1954 | Kelsey |
| 2,744,251 A | 5/1956 | Vollmer |
| 2,790,341 A | 4/1957 | Keep et al. |
| 2,817,339 A | 12/1957 | Sullivan |
| 2,825,162 A | 3/1958 | Flood |
| 2,881,762 A | 4/1959 | Lowrie |
| 2,910,067 A | 10/1959 | White |
| 3,068,870 A | 12/1962 | Levin |
| 3,077,812 A | 2/1963 | Dietrich |
| 3,103,666 A | 9/1963 | Bone |
| 3,123,077 A | 3/1964 | Alcamo |
| 3,209,754 A | 10/1965 | Brown |
| 3,221,746 A | 12/1965 | Noble |
| 3,470,834 A | 10/1969 | Bone |
| 3,527,223 A | 9/1970 | Shein |
| 3,570,497 A | 3/1971 | Lemole |
| 3,577,837 A | 5/1971 | Bader, Jr. |
| 3,579,831 A | 5/1971 | Stevens et al. |
| 3,643,851 A | 2/1972 | Green et al. |
| 3,687,138 A | 8/1972 | Jarvik |
| 3,716,058 A | 2/1973 | Tanner, Jr. |
| 3,717,294 A | 2/1973 | Green |
| 3,757,629 A | 9/1973 | Schneider |
| 3,777,538 A | 12/1973 | Weatherly et al. |
| 3,837,555 A | 9/1974 | Green |
| 3,845,772 A | 11/1974 | Smith |
| 3,875,648 A | 4/1975 | Bone |
| 3,960,147 A | 6/1976 | Murray |
| 3,976,079 A | 8/1976 | Samuels et al. |
| 4,014,492 A | 3/1977 | Rothfuss |
| 4,127,227 A | 11/1978 | Green |
| 4,259,959 A | 4/1981 | Walker |
| 4,263,903 A | 4/1981 | Griggs |
| 4,265,226 A | 5/1981 | Cassimally |
| 4,317,451 A | 3/1982 | Cerwin et al. |
| 4,400,833 A | 8/1983 | Kurland |
| 4,422,567 A | 12/1983 | Haynes |
| 4,454,875 A | 6/1984 | Pratt et al. |
| 4,480,641 A | 11/1984 | Failla et al. |
| 4,485,816 A | 12/1984 | Krumme |
| 4,526,174 A | 7/1985 | Froehlich |
| 4,549,545 A | 10/1985 | Levy |
| 4,570,623 A | 2/1986 | Ellison et al. |
| 4,595,007 A | 6/1986 | Mericle |
| 4,624,254 A | 11/1986 | McGarry et al. |
| 4,627,437 A | 12/1986 | Bedi et al. |
| 4,632,100 A | 12/1986 | Somers et al. |
| 4,635,637 A | 1/1987 | Schreiber |
| 4,669,473 A | 6/1987 | Richards et al. |
| 4,696,300 A | 9/1987 | Anderson |
| 4,719,917 A | 1/1988 | Barrows et al. |
| 4,738,255 A | 4/1988 | Goble et al. |
| 4,741,330 A | 5/1988 | Hayhurst |
| 4,762,260 A | 8/1988 | Richards et al. |
| 4,799,495 A | 1/1989 | Hawkins et al. |
| 4,809,695 A | 3/1989 | Gwathmey et al. |
| 4,851,005 A | 7/1989 | Hunt et al. |
| 4,858,608 A | 8/1989 | McQuilkin |
| 4,884,572 A | 12/1989 | Bays et al. |
| 4,887,601 A | 12/1989 | Richards |
| 4,924,866 A | 5/1990 | Yoon |
| 4,930,674 A | 6/1990 | Barak |
| 4,968,315 A | 11/1990 | Gatturna |
| 4,976,715 A | 12/1990 | Bays et al. |
| 4,994,073 A | 2/1991 | Green |
| 4,997,436 A | 3/1991 | Oberlander |
| 5,002,563 A | 3/1991 | Pyka et al. |
| 5,013,316 A | 5/1991 | Goble et al. |
| 5,015,249 A | 5/1991 | Nakao et al. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,053,047 A | 10/1991 | Yoon |
| 5,059,206 A | 10/1991 | Winters |
| 5,062,563 A | 11/1991 | Green et al. |
| 5,100,417 A | 3/1992 | Cerier et al. |
| 5,102,421 A | 4/1992 | Anspach, Jr. |
| 5,116,357 A | 5/1992 | Eberbach |
| 5,122,155 A | 6/1992 | Eberbach |
| 5,123,913 A | 6/1992 | Wilk et al. |
| RE34,021 E | 8/1992 | Mueller et al. |
| 5,141,515 A | 8/1992 | Eberbach |
| 5,141,520 A | 8/1992 | Goble et al. |
| 5,156,609 A | 10/1992 | Nakao et al. |
| 5,156,616 A | 10/1992 | Meadows et al. |
| 5,167,665 A | 12/1992 | McKinney |
| 5,171,259 A | 12/1992 | Inoue |
| 5,174,295 A | 12/1992 | Christian et al. |
| 5,174,487 A | 12/1992 | Rothfuss et al. |
| 5,176,682 A | 1/1993 | Chow |
| 5,176,692 A | 1/1993 | Wilk et al. |
| 5,203,787 A | 4/1993 | Noblitt et al. |
| 5,217,472 A | 6/1993 | Green et al. |
| 5,224,946 A | 7/1993 | Hayhurst et al. |
| 5,238,004 A | 8/1993 | Sahatjian et al. |
| 5,242,457 A | 9/1993 | Akopov et al. |
| 5,246,441 A | 9/1993 | Ross et al. |
| 5,251,642 A | 10/1993 | Handlos |
| 5,261,914 A | 11/1993 | Warren |
| 5,269,753 A | 12/1993 | Wilk |
| 5,269,783 A | 12/1993 | Sander |
| 5,282,829 A | 2/1994 | Hermes |
| 5,289,963 A | 3/1994 | McGarry et al. |
| 5,290,217 A | 3/1994 | Campos |
| 5,304,187 A | 4/1994 | Green et al. |
| 5,333,624 A | 8/1994 | Tovey |
| 5,342,396 A | 8/1994 | Cook |
| 5,350,400 A | 9/1994 | Esposito et al. |
| 5,352,229 A | 10/1994 | Goble et al. |
| 5,354,292 A | 10/1994 | Braeuer et al. |
| 5,354,302 A | 10/1994 | Ko |
| 5,364,408 A | 11/1994 | Gordon |
| 5,366,460 A | 11/1994 | Eberbach |

(56) References Cited

U.S. PATENT DOCUMENTS

| | | |
|---|---|---|
| 5,370,650 A | 12/1994 | Tovey et al. |
| 5,372,604 A | 12/1994 | Trott |
| 5,380,334 A | 1/1995 | Torrie et al. |
| 5,383,477 A | 1/1995 | DeMatteis |
| 5,397,332 A | 3/1995 | Kammerer et al. |
| 5,403,326 A | 4/1995 | Harrison et al. |
| 5,405,360 A | 4/1995 | Tovey |
| 5,411,522 A | 5/1995 | Trott |
| 5,411,523 A | 5/1995 | Goble |
| 5,417,691 A | 5/1995 | Hayhurst |
| 5,417,712 A | 5/1995 | Whittaker et al. |
| 5,425,490 A | 6/1995 | Goble et al. |
| 5,441,502 A | 8/1995 | Bartlett |
| 5,441,508 A | 8/1995 | Gazielly et al. |
| 5,453,090 A | 9/1995 | Martinez et al. |
| 5,456,720 A | 10/1995 | Schultz et al. |
| 5,464,403 A | 11/1995 | Kieturakis et al. |
| 5,478,354 A | 12/1995 | Tovey et al. |
| 5,482,864 A | 1/1996 | Knobel |
| 5,486,197 A | 1/1996 | Le et al. |
| 5,497,933 A | 3/1996 | DeFonzo et al. |
| 5,500,000 A | 3/1996 | Feagin et al. |
| 5,501,695 A | 3/1996 | Anspach, Jr. et al. |
| 5,503,623 A | 4/1996 | Tilton, Jr. |
| 5,505,735 A | 4/1996 | Li |
| 5,507,754 A | 4/1996 | Green et al. |
| 5,520,700 A | 5/1996 | Beyar et al. |
| 5,522,817 A | 6/1996 | Sander et al. |
| 5,545,180 A | 8/1996 | Le et al. |
| 5,560,532 A | 10/1996 | DeFonzo et al. |
| 5,562,689 A | 10/1996 | Green et al. |
| 5,569,306 A | 10/1996 | Thal |
| 5,582,616 A | 12/1996 | Bolduc et al. |
| 5,584,835 A | 12/1996 | Greenfield |
| 5,618,314 A | 4/1997 | Harwin et al. |
| 5,622,257 A | 4/1997 | Deschenes et al. |
| 5,628,751 A | 5/1997 | Sander et al. |
| 5,643,319 A | 7/1997 | Green et al. |
| 5,643,321 A | 7/1997 | McDevitt |
| 5,647,874 A | 7/1997 | Hayhurst |
| 5,649,963 A | 7/1997 | McDevitt |
| 5,662,683 A | 9/1997 | Kay |
| 5,667,513 A | 9/1997 | Torrie et al. |
| 5,674,245 A | 10/1997 | Ilgen |
| 5,681,342 A | 10/1997 | Benchetrit |
| 5,702,215 A | 12/1997 | Li |
| 5,713,903 A | 2/1998 | Sander et al. |
| 5,720,753 A | 2/1998 | Sander et al. |
| 5,725,541 A | 3/1998 | Anspach, III et al. |
| 5,741,282 A | 4/1998 | Anspach, III et al. |
| 5,766,246 A | 6/1998 | Mulhauser et al. |
| 5,782,864 A | 7/1998 | Lizardi |
| 5,797,909 A | 8/1998 | Michelson |
| 5,797,931 A | 8/1998 | Bito et al. |
| 5,797,963 A | 8/1998 | McDevitt |
| 5,807,403 A | 9/1998 | Beyar et al. |
| 5,830,221 A | 11/1998 | Stein et al. |
| 5,836,961 A | 11/1998 | Kieturakis et al. |
| 5,868,762 A | 2/1999 | Cragg et al. |
| 5,873,891 A | 2/1999 | Sohn |
| 5,885,258 A | 3/1999 | Sachdeva et al. |
| 5,885,294 A | 3/1999 | Pedlick et al. |
| 5,893,856 A | 4/1999 | Jacob et al. |
| 5,904,696 A | 5/1999 | Rosenman |
| 5,919,184 A | 7/1999 | Tilton, Jr. |
| 5,922,026 A | 7/1999 | Chin |
| 5,928,244 A | 7/1999 | Tovey et al. |
| 5,948,000 A | 9/1999 | Larsen et al. |
| 5,957,939 A | 9/1999 | Heaven et al. |
| 5,957,953 A | 9/1999 | Dipoto et al. |
| 5,968,044 A | 10/1999 | Nicholson et al. |
| 5,980,557 A | 11/1999 | Iserin et al. |
| 5,989,265 A | 11/1999 | Bouquet De La Joliniere et al. |
| 5,997,552 A | 12/1999 | Person et al. |
| 6,063,088 A | 5/2000 | Winslow |
| 6,099,518 A | 8/2000 | Adams et al. |
| 6,156,045 A | 12/2000 | Ulbrich et al. |
| 6,179,840 B1 | 1/2001 | Bowman |
| 6,193,731 B1 | 2/2001 | Oppelt et al. |
| 6,193,733 B1 | 2/2001 | Adams |
| 6,245,072 B1 | 6/2001 | Zdeblick et al. |
| 6,302,885 B1 | 10/2001 | Essiger |
| 6,312,442 B1 | 11/2001 | Kieturakis et al. |
| 6,315,789 B1 | 11/2001 | Cragg |
| 6,318,616 B1 | 11/2001 | Pasqualucci et al. |
| 6,322,563 B1 | 11/2001 | Cummings et al. |
| 6,325,805 B1 | 12/2001 | Ogilvie et al. |
| 6,387,113 B1 | 5/2002 | Hawkins et al. |
| 6,391,333 B1 | 5/2002 | Li et al. |
| 6,413,274 B1 | 7/2002 | Pedros |
| 6,425,900 B1 | 7/2002 | Knodel et al. |
| 6,436,110 B2 | 8/2002 | Bowman et al. |
| 6,447,522 B2 | 9/2002 | Gambale et al. |
| 6,447,524 B1 | 9/2002 | Knodel et al. |
| 6,478,803 B1 | 11/2002 | Kapec et al. |
| 6,482,178 B1 | 11/2002 | Andrews et al. |
| 6,482,210 B1 | 11/2002 | Skiba et al. |
| 6,506,190 B1 | 1/2003 | Walshe |
| 6,508,803 B1 | 1/2003 | Horikawa et al. |
| 6,511,499 B2 | 1/2003 | Schmieding et al. |
| 6,517,564 B1 | 2/2003 | Grafton et al. |
| 6,524,316 B1 | 2/2003 | Nicholson et al. |
| 6,527,795 B1 | 3/2003 | Lizardi |
| 6,530,933 B1 | 3/2003 | Yeung et al. |
| 6,540,769 B1 | 4/2003 | Miller, III |
| 6,551,333 B2 | 4/2003 | Kuhns et al. |
| 6,554,852 B1 | 4/2003 | Oberlander |
| 6,569,186 B1 | 5/2003 | Winters et al. |
| 6,575,976 B2 | 6/2003 | Grafton |
| 6,599,286 B2 | 7/2003 | Campin et al. |
| 6,620,185 B1 | 9/2003 | Harvie et al. |
| 6,629,988 B2 | 10/2003 | Weadock |
| 6,638,297 B1 | 10/2003 | Huitema |
| 6,639,365 B2 | 10/2003 | Pruett |
| 6,648,893 B2 | 11/2003 | Dudasik |
| 6,666,672 B1 | 12/2003 | Steffens |
| 6,666,872 B2 | 12/2003 | Barreiro et al. |
| 6,673,094 B1 | 1/2004 | McDevitt et al. |
| 6,685,728 B2 | 2/2004 | Sinnott et al. |
| 6,692,506 B1 | 2/2004 | Ory et al. |
| 6,723,099 B1 | 4/2004 | Goshert |
| 6,726,704 B1 | 4/2004 | Loshakove et al. |
| 6,726,705 B2 | 4/2004 | Peterson et al. |
| 6,740,100 B2 | 5/2004 | Demopulos et al. |
| 6,746,472 B2 | 6/2004 | Frazier et al. |
| 6,764,500 B1 | 7/2004 | Muijs Van De Moer et al. |
| 6,770,073 B2 | 8/2004 | McDevitt et al. |
| 6,779,701 B2 | 8/2004 | Bailly et al. |
| 6,800,081 B2 | 10/2004 | Parodi |
| 6,835,206 B2 | 12/2004 | Jackson |
| 6,849,078 B2 | 2/2005 | Durgin et al. |
| 6,887,259 B2 | 5/2005 | Lizardi |
| 6,926,723 B1 | 8/2005 | Mulhauser et al. |
| 6,932,834 B2 | 8/2005 | Lizardi et al. |
| 6,939,365 B1 | 9/2005 | Fogarty et al. |
| 6,946,003 B1 | 9/2005 | Wolowacz et al. |
| 6,949,117 B2 | 9/2005 | Gambale et al. |
| 6,964,685 B2 | 11/2005 | Murray et al. |
| 6,966,916 B2 | 11/2005 | Kumar |
| 6,972,027 B2 | 12/2005 | Fallin et al. |
| 6,984,241 B2 | 1/2006 | Lubbers et al. |
| 6,991,597 B2 | 1/2006 | Gellman et al. |
| 7,008,435 B2 | 3/2006 | Cummins |
| 7,021,316 B2 | 4/2006 | Leiboff |
| 7,025,772 B2 | 4/2006 | Gellman et al. |
| 7,033,379 B2 | 4/2006 | Peterson |
| 7,037,324 B2 | 5/2006 | Martinek |
| 7,048,171 B2 | 5/2006 | Thornton et al. |
| 7,063,711 B1 | 6/2006 | Oshakove et al. |
| 7,083,638 B2 | 8/2006 | Foerster |
| 7,087,064 B1 | 8/2006 | Hyde |
| 7,112,214 B2 | 9/2006 | Peterson et al. |
| 7,118,581 B2 | 10/2006 | Friden |
| 7,144,403 B2 | 12/2006 | Booth |

(56) References Cited

U.S. PATENT DOCUMENTS

| | | |
|---|---|---|
| 7,144,413 B2 | 12/2006 | Wilford et al. |
| 7,144,414 B2 | 12/2006 | Harvie et al. |
| 7,150,750 B2 | 12/2006 | Damarati |
| 7,153,314 B2 | 12/2006 | Laufer et al. |
| 7,160,314 B2 | 1/2007 | Sgro et al. |
| 7,160,326 B2 | 1/2007 | Ball |
| 7,163,551 B2 | 1/2007 | Anthony et al. |
| 7,163,563 B2 | 1/2007 | Schwartz et al. |
| 7,169,157 B2 | 1/2007 | Kayan |
| 7,189,251 B2 | 3/2007 | Kay |
| 7,201,754 B2 | 4/2007 | Stewart et al. |
| 7,214,232 B2 | 5/2007 | Bowman et al. |
| 7,226,469 B2 | 6/2007 | Benavitz et al. |
| 7,229,452 B2 | 6/2007 | Kayan |
| 7,247,164 B1 | 7/2007 | Ritchart et al. |
| 7,303,577 B1 | 12/2007 | Dean |
| 7,309,337 B2 | 12/2007 | Colleran et al. |
| 7,320,692 B1 | 1/2008 | Bender et al. |
| 7,320,701 B2 | 1/2008 | Haut et al. |
| 7,322,935 B2 | 1/2008 | Palmer et al. |
| 7,326,231 B2 | 2/2008 | Phillips et al. |
| 7,343,920 B2 | 3/2008 | Toby et al. |
| 7,368,124 B2 | 5/2008 | Chun et al. |
| 7,377,934 B2 | 5/2008 | Lin et al. |
| 7,381,213 B2 | 6/2008 | Lizardi |
| 7,390,329 B2 | 6/2008 | Westra et al. |
| 7,399,304 B2 | 7/2008 | Gambale et al. |
| 7,404,824 B1 | 7/2008 | Webler et al. |
| 7,416,554 B2 | 8/2008 | Lam et al. |
| 7,452,368 B2 | 11/2008 | Liberatore et al. |
| 7,460,913 B2 | 12/2008 | Kuzma et al. |
| 7,463,933 B2 | 12/2008 | Wahlstrom et al. |
| 7,465,308 B2 | 12/2008 | Sikora et al. |
| 7,481,832 B1 | 1/2009 | Meridew et al. |
| 7,485,124 B2 | 2/2009 | Kuhns et al. |
| 7,497,854 B2 | 3/2009 | Gill et al. |
| 7,500,972 B2 | 3/2009 | Voegele et al. |
| 7,500,980 B2 | 3/2009 | Gill et al. |
| 7,500,983 B1 | 3/2009 | Kaiser et al. |
| 7,503,474 B2 | 3/2009 | Hillstead et al. |
| 7,506,791 B2 | 3/2009 | Omaits et al. |
| 7,559,941 B2 | 7/2009 | Zannis et al. |
| 7,572,276 B2 | 8/2009 | Lim et al. |
| 7,585,311 B2 | 9/2009 | Green et al. |
| 7,766,208 B2 | 8/2010 | Epperly et al. |
| 7,771,440 B2 | 8/2010 | Ortiz et al. |
| 7,776,057 B2 | 8/2010 | Laufer et al. |
| 7,780,685 B2 | 8/2010 | Hunt et al. |
| 7,785,255 B2 | 8/2010 | Malkani |
| 7,807,192 B2 | 10/2010 | Li et al. |
| 7,819,880 B2 | 10/2010 | Zannis et al. |
| 7,846,171 B2 | 12/2010 | Kullas et al. |
| 7,867,222 B1 | 1/2011 | Tilton, Jr. et al. |
| 7,918,879 B2 | 4/2011 | Yeung et al. |
| 8,114,101 B2 | 2/2012 | Criscuolo et al. |
| 8,197,837 B2 | 6/2012 | Jamiolkowski et al. |
| 8,221,440 B2 | 7/2012 | Kullas et al. |
| 8,585,773 B1 * | 11/2013 | Kucklick ............ A61B 17/34 623/23.72 |
| 8,668,718 B2 | 3/2014 | Euteneuer et al. |
| 8,763,878 B2 | 7/2014 | Euteneuer et al. |
| 8,821,536 B2 | 9/2014 | Euteneuer et al. |
| 8,821,537 B2 | 9/2014 | Euteneuer et al. |
| 8,968,329 B2 | 3/2015 | Cabrera |
| 9,033,201 B2 | 5/2015 | Euteneuer |
| 9,095,337 B2 | 8/2015 | Euteneuer et al. |
| 9,101,460 B2 | 8/2015 | Euteneuer et al. |
| 9,107,661 B2 | 8/2015 | Euteneuer et al. |
| 9,113,977 B2 | 8/2015 | Euteneuer et al. |
| 9,125,650 B2 | 9/2015 | Euteneuer et al. |
| 9,179,910 B2 | 11/2015 | Euteneuer et al. |
| 9,179,961 B2 | 11/2015 | Euteneuer et al. |
| 9,198,751 B2 | 12/2015 | Euteneuer et al. |
| 9,204,940 B2 | 12/2015 | Euteneuer et al. |
| 9,247,978 B2 | 2/2016 | Euteneuer et al. |
| 9,271,726 B2 | 3/2016 | Euteneuer |
| 9,314,314 B2 | 4/2016 | Euteneuer et al. |
| 9,314,331 B2 | 4/2016 | Euteneuer et al. |
| 9,370,356 B2 | 6/2016 | Euteneuer et al. |
| 9,393,103 B2 | 7/2016 | Van Kampen et al. |
| 10,568,622 B2 | 2/2020 | Euteneuer et al. |
| 2002/0077687 A1 | 6/2002 | Ahn |
| 2002/0090725 A1 | 7/2002 | Simpson et al. |
| 2002/0123767 A1 | 9/2002 | Prestel |
| 2002/0165559 A1 | 11/2002 | Grant et al. |
| 2003/0073979 A1 | 4/2003 | Naimark et al. |
| 2003/0125748 A1 | 7/2003 | Li et al. |
| 2003/0212456 A1 | 11/2003 | Lipchitz et al. |
| 2004/0059416 A1 | 3/2004 | Murray et al. |
| 2004/0073219 A1 | 4/2004 | Skiba et al. |
| 2004/0138705 A1 | 7/2004 | Heino et al. |
| 2004/0167519 A1 | 8/2004 | Weiner et al. |
| 2005/0015021 A1 | 1/2005 | Shiber |
| 2005/0049618 A1 | 3/2005 | Masuda et al. |
| 2005/0051597 A1 | 3/2005 | Toledano |
| 2005/0059996 A1 | 3/2005 | Bauman et al. |
| 2005/0060033 A1 | 3/2005 | Vacanti et al. |
| 2005/0107807 A1 | 5/2005 | Nakao |
| 2005/0113736 A1 | 5/2005 | Orr et al. |
| 2005/0171569 A1 | 8/2005 | Girard et al. |
| 2005/0187576 A1 | 8/2005 | Whitman et al. |
| 2005/0234298 A1 | 10/2005 | Kucklick |
| 2005/0240222 A1 | 10/2005 | Shipp |
| 2005/0274768 A1 | 12/2005 | Cummins et al. |
| 2006/0074423 A1 | 4/2006 | Alleyne et al. |
| 2006/0178743 A1 | 8/2006 | Carter |
| 2006/0235442 A1 | 10/2006 | Huitema |
| 2006/0293760 A1 | 12/2006 | DeDeyne |
| 2007/0078477 A1 | 4/2007 | Heneveld, Sr. et al. |
| 2007/0083236 A1 | 4/2007 | Sikora et al. |
| 2007/0112361 A1 | 5/2007 | Schonholz et al. |
| 2007/0179531 A1 | 8/2007 | Thornes |
| 2007/0185506 A1 | 8/2007 | Jackson |
| 2007/0190108 A1 | 8/2007 | Datta et al. |
| 2007/0219558 A1 | 9/2007 | Deutsch |
| 2007/0270804 A1 | 11/2007 | Chudik |
| 2007/0288023 A1 | 12/2007 | Pellegrino et al. |
| 2008/0027470 A1 | 1/2008 | Hart et al. |
| 2008/0051888 A1 | 2/2008 | Ratcliffe et al. |
| 2008/0065153 A1 | 3/2008 | Allard et al. |
| 2008/0090936 A1 | 4/2008 | Fujimura et al. |
| 2008/0125644 A1 | 5/2008 | Lubock et al. |
| 2008/0125766 A1 | 5/2008 | Lubock et al. |
| 2008/0125869 A1 | 5/2008 | Paz et al. |
| 2008/0135600 A1 | 6/2008 | Hiranuma et al. |
| 2008/0173691 A1 | 7/2008 | Mas et al. |
| 2008/0188874 A1 | 8/2008 | Henderson |
| 2008/0188936 A1 | 8/2008 | Ball et al. |
| 2008/0195119 A1 | 8/2008 | Ferree |
| 2008/0200949 A1 | 8/2008 | Hiles et al. |
| 2008/0241213 A1 | 10/2008 | Chun et al. |
| 2008/0272173 A1 | 11/2008 | Coleman et al. |
| 2008/0294174 A1 | 11/2008 | Bardsley et al. |
| 2008/0306408 A1 | 12/2008 | Lo |
| 2009/0001122 A1 | 1/2009 | Prommersberger et al. |
| 2009/0012521 A1 | 1/2009 | Axelson, Jr. et al. |
| 2009/0030434 A1 | 1/2009 | Paz et al. |
| 2009/0069806 A1 | 3/2009 | De La Mora Levy et al. |
| 2009/0076541 A1 | 3/2009 | Chin et al. |
| 2009/0105535 A1 | 4/2009 | Green et al. |
| 2009/0112085 A1 | 4/2009 | Eby |
| 2009/0134198 A1 | 5/2009 | Knodel et al. |
| 2009/0156986 A1 | 6/2009 | Trenhaile |
| 2009/0156997 A1 | 6/2009 | Trenhaile |
| 2009/0182245 A1 | 7/2009 | Zambelli |
| 2009/0242609 A1 | 10/2009 | Kanner |
| 2009/0299401 A1 | 12/2009 | Tilson |
| 2010/0145367 A1 | 6/2010 | Ratcliffe |
| 2010/0147922 A1 | 6/2010 | Olson |
| 2010/0163598 A1 | 7/2010 | Belzer |
| 2010/0191332 A1 | 7/2010 | Euteneuer et al. |
| 2010/0241227 A1 | 9/2010 | Euteneuer et al. |
| 2010/0249801 A1 | 9/2010 | Sengun et al. |
| 2010/0256675 A1 | 10/2010 | Romans |

(56) References Cited

U.S. PATENT DOCUMENTS

| | | |
|---|---|---|
| 2010/0274278 A1 | 10/2010 | Fleenor et al. |
| 2010/0292715 A1 | 11/2010 | Nering et al. |
| 2010/0292791 A1 | 11/2010 | Lu et al. |
| 2010/0312250 A1 | 12/2010 | Euteneuer et al. |
| 2010/0312275 A1 | 12/2010 | Euteneuer et al. |
| 2010/0327042 A1 | 12/2010 | Amid et al. |
| 2011/0000950 A1 | 1/2011 | Euteneuer et al. |
| 2011/0004221 A1 | 1/2011 | Euteneuer et al. |
| 2011/0011917 A1 | 1/2011 | Loulmet |
| 2011/0034942 A1 | 2/2011 | Levin et al. |
| 2011/0040310 A1 | 2/2011 | Levin et al. |
| 2011/0040311 A1 | 2/2011 | Levin et al. |
| 2011/0054485 A1 | 3/2011 | Kullas et al. |
| 2011/0066166 A1 | 3/2011 | Levin et al. |
| 2011/0106154 A1 | 5/2011 | DiMatteo et al. |
| 2011/0114700 A1 | 5/2011 | Baxter, III et al. |
| 2011/0224702 A1 | 9/2011 | Van Kampen et al. |
| 2011/0264149 A1 | 10/2011 | Pappalardo et al. |
| 2012/0100200 A1 | 4/2012 | Belcheva et al. |
| 2012/0160893 A1 | 6/2012 | Harris et al. |
| 2012/0193391 A1 | 8/2012 | Michler et al. |
| 2012/0209401 A1 | 8/2012 | Euteneuer et al. |
| 2012/0211543 A1 | 8/2012 | Euteneuer |
| 2012/0248171 A1 | 10/2012 | Bailly et al. |
| 2012/0316608 A1 | 12/2012 | Foley |
| 2013/0053825 A1 | 2/2013 | Moulton et al. |
| 2013/0110156 A1 | 5/2013 | Nakayama et al. |
| 2013/0153627 A1 | 6/2013 | Euteneuer et al. |
| 2013/0153628 A1 | 6/2013 | Euteneuer |
| 2013/0158554 A1 | 6/2013 | Euteneuer et al. |
| 2013/0158587 A1 | 6/2013 | Euteneuer et al. |
| 2013/0158661 A1 | 6/2013 | Euteneuer et al. |
| 2013/0172920 A1 | 7/2013 | Euteneuer et al. |
| 2013/0172997 A1 | 7/2013 | Euteneuer et al. |
| 2013/0184716 A1 | 7/2013 | Euteneuer et al. |
| 2013/0240598 A1 | 9/2013 | Euteneuer et al. |
| 2013/0245627 A1 | 9/2013 | Euteneuer et al. |
| 2013/0245682 A1 | 9/2013 | Euteneuer et al. |
| 2013/0245683 A1 | 9/2013 | Euteneuer et al. |
| 2013/0245706 A1 | 9/2013 | Euteneuer et al. |
| 2013/0245707 A1 | 9/2013 | Euteneuer et al. |
| 2013/0245762 A1 | 9/2013 | Van Kampen et al. |
| 2013/0245774 A1 | 9/2013 | Euteneuer et al. |
| 2016/0113644 A1 | 4/2016 | Diduch et al. |

FOREIGN PATENT DOCUMENTS

| | | |
|---|---|---|
| EP | 0142225 A1 | 5/1985 |
| EP | 0298400 A1 | 1/1989 |
| EP | 0390613 A1 | 10/1990 |
| EP | 0543499 A1 | 5/1993 |
| EP | 0548998 A1 | 6/1993 |
| EP | 0557963 A1 | 9/1993 |
| EP | 0589306 A2 | 3/1994 |
| EP | 0908152 A1 | 4/1999 |
| EP | 1114618 A2 | 7/2001 |
| EP | 1491157 A1 | 12/2004 |
| EP | 1559379 A1 | 8/2005 |
| EP | 2030576 A2 | 3/2009 |
| EP | 2097021 A2 | 9/2009 |
| GB | 2154688 A | 9/1985 |
| GB | 2397240 A | 7/2004 |
| JP | 58188442 A | 11/1983 |
| JP | 2005586122 A | 3/2005 |
| JP | 2006515774 A | 6/2006 |
| JP | 2007175297 A | 7/2007 |
| JP | 2012528703 A | 11/2012 |
| JP | 2014524333 A | 9/2014 |
| WO | 8505025 A1 | 11/1985 |
| WO | 0176456 A2 | 10/2001 |
| WO | 0191644 A1 | 12/2001 |
| WO | 0234140 A2 | 5/2002 |
| WO | 2003105670 A2 | 12/2003 |
| WO | 2004000138 A1 | 12/2003 |
| WO | 2004093690 A1 | 11/2004 |
| WO | 2005016389 A2 | 2/2005 |
| WO | 2006086679 A1 | 8/2006 |
| WO | 2007014910 A1 | 2/2007 |
| WO | 2007030676 A2 | 3/2007 |
| WO | 2007078978 A2 | 7/2007 |
| WO | 2007082088 A2 | 7/2007 |
| WO | 2008063636 A2 | 5/2008 |
| WO | 2008111073 A2 | 9/2008 |
| WO | 2008111078 A2 | 9/2008 |
| WO | 2008139473 A2 | 11/2008 |
| WO | 2009079211 A1 | 6/2009 |
| WO | 2009143331 A1 | 11/2009 |
| WO | 2010081029 A1 | 7/2010 |
| WO | 2010141906 A1 | 12/2010 |
| WO | 2011095890 A2 | 8/2011 |
| WO | 2011128903 A2 | 10/2011 |
| WO | 2011140382 A1 | 11/2011 |
| WO | 20130101638 A1 | 7/2013 |

OTHER PUBLICATIONS

Invitation to Pay Additional Fees, for International Application No. PCT/US2016/030949, 7 pages, date mailed Aug. 10, 2016.

Office Action Application No. 2017-556679, 10 pages, date mailed Jun. 19, 2018.

"Rotator Cuff Tear," Wikipedia, the free encyclopedia, 14 pages, Downloaded on Dec. 6, 2012.

Alexander et al., "Ligament and tendon repair with an absorbable polymer-coated carbon fiber stent," Bulletin of the Hospital for Joint Diseases Orthopaedic Institute, 46(2):155-173, 1986.

Bahler et al., "Trabecular bypass stents decrease intraocular pressure in cultured himan anterior segments," Am. J. Opthamology, 138(6):988-994, Dec. 2004.

Chamay et al., "Digital contracture deformity after implantation of a silicone prosthesis: Light and electron microscopic study," The Journal of Hand Surgery, 3(3):266-270, May 1978.

D'Ermo et al., "Our results of the operation of ab externo," Opthalmologica, 168: 347-355, 1971.

France et al., "Biomechanical evaluation of rotator cuff fixation methods," The American Journal of Sports Medicine, 17(2), 1989.

Goodship et al., "An assessment of filamentous carbon fibre for the treatment of tendon injury in the horse," Veterinary Record, 106: 217-221, Mar. 8, 1980.

Hunter et al., "Flexor-tendon reconstruction in severely damaged hands," The Journal of Bone and Joint Surgery (American Volume), 53-A(5): 329-358, Jul. 1971.

Johnstone et al., "Microsurgery of Schlemm's canal and the human aqueous outflow system," Am. J. Opthamology, 76(6): 906-917, Dec. 1973.

Kowalsky et al., "Evaluation of suture abrasion against rotator cuff tendon and proximal humerus bone," Arthroscopy: The Journal of Arthroscopic and Related Surgery, 24(3):329-334, Mar. 2008.

Lee et al., "Aqueous-venous and intraocular pressure. Preliminary report of animal studies," Investigative Opthalmology, 5(1): 59-64, Feb. 1966.

Maepea et al., "The pressures in the episcleral veins, Schlemm's canal and the trabecular meshwork in monkeys: Effects of changes in intraocular pressure," Exp. Eye Res., 49:645-663, 1989.

Nicolle et al., "A silastic tendon prosthesis as an adjunct to flexor tendon grafting: An experimental and clinical evaluation," British Journal of Plastic Surgery, 22(3-4):224-236, 1969.

Rubin et al., "The use of acellular biologic tissue patches in foot and ankle surgery," Clinics in Podiatric Medicine and Surgery, 22:533-552, 2005.

Schultz, "Canaloplasty procedure shows promise for open-angle glaucoma in European study," Ocular Surgery News, 34-35, Mar. 1, 2007.

Spiegel et al., "Schlemm's canal implant: a new method to lower intraocular pressure in patients with POAG," Opthalmic Surgery and Lasers, 30(6):492-494, Jun. 1999.

Stenson et al., "Arthroscopic treatment of partial rotator cuff tears," Operative Techniques in Sports Medicine, 12 (2):135-148, Apr. 2004.

(56) References Cited

OTHER PUBLICATIONS

Valdez et al., "Repair of digital flexor tendon lacerations in the horse, using carbon fiber implants," JAYMA, 177(5): 427-435, Sep. 1, 1980.

* cited by examiner

MEDICAL IMPLANT DELIVERY SYSTEM AND RELATED METHODS

CROSS REFERENCE TO RELATED APPLICATIONS

This application is a continuation of U.S. patent application Ser. No. 17/138,324, filed Dec. 30, 2020, which is a continuation of U.S. patent application Ser. No. 15/147,106, filed May 5, 2016, which claims the benefit of priority under 35 U.S.C. § 119 to U.S. Provisional Application Ser. No. 62/157,674, filed May 6, 2015, the entirety of which are incorporated herein by reference.

TECHNICAL FIELD

The present disclosure pertains generally, but not by way of limitation, to medical devices, and methods for manufacturing medical devices. More particularly, the present disclosure pertains to devices for introducing and positioning implants within patients, and methods for manufacturing and using such devices.

BACKGROUND

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. Adequate procedures do not exist for repairing a partial thickness tear of less than 50% in the supraspinatus tendon. Current procedures attempt to alleviate impingement or make room for movement of the tendon to prevent further damage and relieve discomfort but do not repair or strengthen the tendon. Use of the still damaged tendon can lead to further damage or injury. There is an ongoing need to deliver and adequately position medical implants during an arthroscopic procedure in order to treat injuries to the rotator cuff, rotator cuff tendons, or other soft tissue or tendon injuries throughout a body.

BRIEF SUMMARY

The disclosure describes various medical devices and methods for using medical devices to assist in delivering and positioning implants within a body. In a first example, an implant delivery system may comprise a sheath member having a distal end, a proximal end, and a central longitudinal axis, the sheath member defining a lumen along the central longitudinal axis and an implant delivery shaft having a distal end and a proximal end, where the implant delivery shaft disposed at least partially within the sheath member. In some examples, the implant delivery system may additionally include an implant spreader assembly disposed at the distal end of the implant delivery shaft and a cap disposed at the distal end of the sheath member, where the cap obstructs at least a portion of an opening into the lumen of the sheath member.

Alternatively, or additionally, in the above example, the cap may comprise a plurality of petals.

Alternatively, or additionally, in any of the above examples, the cap may comprise an even number of petals.

Alternatively, or additionally, in any of the above examples, each of the plurality of petals may be disposed opposite another of the plurality of petals.

Alternatively, or additionally, in any of the above examples, the cap may comprise six petals.

Alternatively, or additionally, in any of the above examples, the petals are configured to collapse together when inserted into tissue.

Alternatively, or additionally, in any of the above examples, when collapsed together, the petals form a plug and prevent tissue from entering the lumen of the sheath member as the implant delivery system is advanced into the tissue.

Alternatively, or additionally, in any of the above examples, each of the petals may comprise a recessed portion.

Alternatively, or additionally, in any of the above examples, the petals may curve inward toward the central longitudinal axis.

Alternatively, or additionally, in any of the above examples, at least a portion of the opening into the lumen may be unobstructed by the cap.

Alternatively, or additionally, in any of the above examples, at least a portion of the cap may be disposed at least partially within the lumen of the sheath member.

Alternatively, or additionally, in any of the above examples, the cap may be tethered to the sheath member.

Alternatively, or additionally, in any of the above examples, the distal end of the sheath member may be angled.

Alternatively, or additionally, in any of the above examples, the cap may be hingedly connected to the sheath member.

Alternatively, or additionally, in any of the above examples, the implant delivery system may further comprise a sealing member disposed on at least a portion of the implant delivery shaft that is disposed within the sheath member.

In another example, an implant delivery system for delivering an implant to a target site may comprise a sheath member having a distal end, a proximal end, and a central longitudinal axis, the sheath member defining a lumen along the central longitudinal axis, and an implant delivery shaft having a distal end and a proximal end, the implant delivery shaft disposed at least partially within the sheath member, wherein the implant delivery shaft comprises a first section with a first diameter, a second section with a second diameter, and a third section with a third diameter, wherein each of the first diameter, second diameter, and third diameter have different values. In some examples, the implant delivery system may additionally include an implant spreader assembly disposed at the distal end of the implant delivery shaft.

Alternatively, or additionally, in the above example, the implant delivery system may further comprise a proximal movement lock engaged with the sheath member and disposed around the implant delivery shaft proximal of the third section of the implant delivery shaft, the proximal movement lock preventing the third section of the implant delivery shaft from being advanced proximal of the proximal movement lock.

Alternatively, or additionally, in any of the above examples, the implant delivery may further comprise a distal movement lock, the distal movement lock having a closed position and an open position, wherein in the closed position the distal movement lock is engaged with the implant delivery shaft and prevents the implant delivery shaft from being advanced distally, and wherein in the open position, the distal movement lock is disengaged from the implant delivery shaft and allows the implant delivery shaft to be advanced distally.

Alternatively, or additionally, in any of the above examples, when distal movement lock is engaged with the implant delivery shaft, the distal movement lock may be engaged along the second section of the implant delivery shaft.

In still another example, a method for delivering a sheet-like implant to a target site may comprise positioning an implant delivery system proximate an incision in a patient, wherein the implant delivery system comprises: a sheath member having a distal end, a proximal end, and a central longitudinal axis, the sheath member defining a lumen along the central longitudinal axis, an implant delivery shaft having a distal end and a proximal end, the implant delivery shaft disposed at least partially within the sheath member, an implant spreader assembly disposed at the distal end of the implant delivery shaft, a sheet-like implant disposed on the implant spreader assembly in a folded configuration, and a cap disposed at the distal end of the sheath member, the cap comprising a plurality of petals and obstructing at least a portion of an opening into the lumen of the sheath member. In some examples, the method may further comprise inserting the implant delivery system into the incision and advancing the implant delivery system to the target implant site. Finally, in some examples, the method may comprise advancing the implant delivery shaft distally, wherein the distal movement of the implant delivery shaft causes at least some of the plurality of petals to expand outward away from the central longitudinal axis, the distal movement further uncovering the implant spreader assembly and the sheet-like implant from within the sheath member, and wherein, when uncovered, the implant spreader assembly unfolds the sheet-like implant from the folded configuration to an unfolded configuration.

Alternatively, or additionally, in the above example, the method may further comprise securing the sheet-like implant to the target site.

Alternatively, or additionally, in any of the above examples, each of the plurality of petals may be disposed opposite another of the plurality of petals.

The above summary of some examples and embodiments is not intended to describe each disclosed embodiment or every implementation of the present disclosure. The Brief Description of the Drawings, and Detailed Description, which follow, more particularly exemplify these embodiments, but are also intended as exemplary and not limiting.

Figure 1:
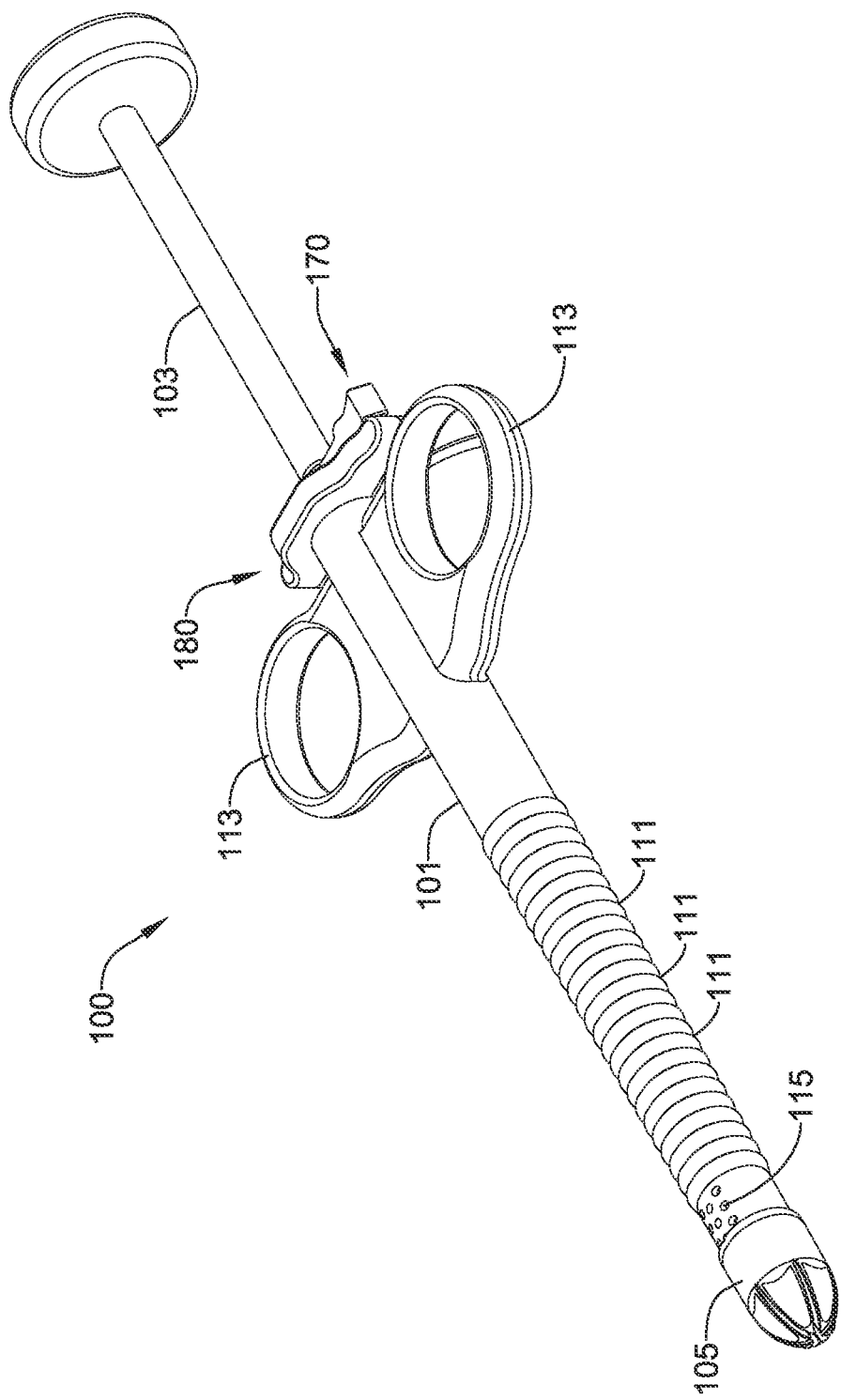
FIG. 1 is perspective view of an exemplary implant delivery system, according to an example of the present disclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

Definitions of certain terms are provided below and shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or able to be arranged with each other to form other additional embodiments or to complement and/or enrich the described embodiment(s), as would be understood by one of ordinary skill in the art.

FIG. 1 provides a perspective view of implant delivery system 100. In at least some embodiments, implant delivery system 100 comprises sheath member 101, implant delivery shaft 103, cap 105, distal movement lock 170, and proximal movement lock 180. Implant delivery system 100 may additionally comprise implant spreader assembly 107 residing within sheath member 101 and connected to implant delivery shaft 103, as depicted in other figures.

Generally, to deliver an implant, such as a sheet-like implant, to a target implant site of a patient, a physician may create an incision in the patient opening into the target implant site. The physician may then insert implant delivery system 100 into the incision and position the proximal end of implant delivery system 100, including cap 105, at the target implant site. The physician may then manipulate implant delivery shaft 103 to force implant spreader assembly 107, including a sheet-like implant, out of sheath member 101, through cap 105, and adjacent to the target implant site. The physician may then attach the sheet-like implant to the target implant site and remove implant delivery system 100 from the patient.

Figure 2:
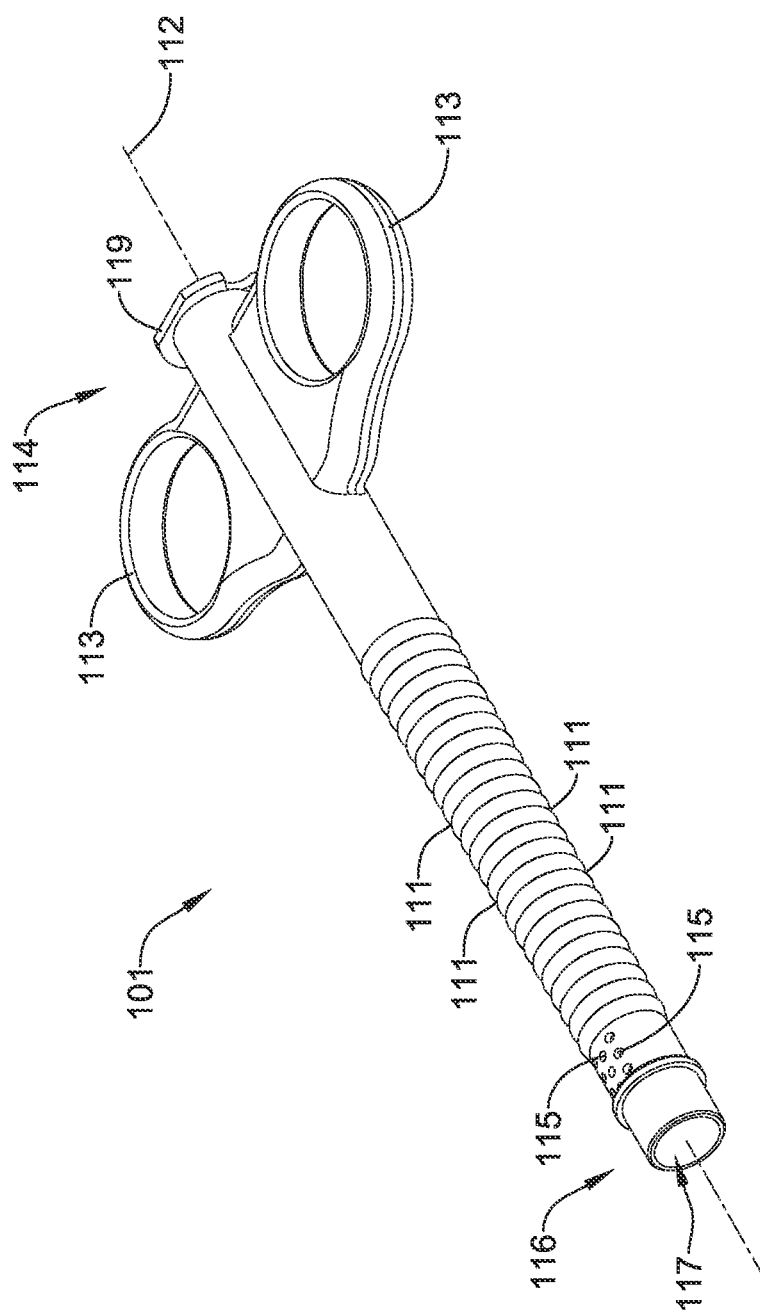
FIG. 2 is perspective view of an exemplary sheath member of the implant delivery system of FIG. 1, according to an example of the present disclosure.

Turning more specifically to sheath member 101, as depicted in FIG. 2, in at least some embodiments, sheath member 101 may include ribs 111, handles 113, holes 115, and flange 119. However, in other embodiments, sheath member 101 may not include one or more of these members or features. For instance, in some embodiments, sheath member 101 may not include ribs 111 or holes 115. In some instances sheath member 101 may be monolithically formed to include ribs 111, handles 113, holes 115, and flange 119. However, in other instances sheath member 101 may be formed of multiple components. Additionally, as can be seen, sheath member 101 extends along central longitudinal axis 112 and defines lumen 117. Sheath member 101 additionally includes openings at both distal end 116 and proximal end 114 of sheath member 101.

Ribs 111 may generally extend away from sheath member 101 in a radially outward direction, or in other embodiments, proximally toward proximal end 114. When implant delivery system 100 is inserted into an incision, ribs 111 may provide a retention force holding implant delivery system 100 within the incision. This feature of ribs 111 may be particularly useful in situations where the target implant site is inflated with one or more injected liquids, which may provide pressure against implant delivery system 100 working to force implant delivery system 100 out of the incision.

Handles 113 are depicted as being attached proximate proximal end 114 of sheath member 101 and are generally circular in shape. However, in other embodiments, handles 113 may be attached to sheath member 101 at other locations and take on other shapes that provide a surface for a user to grasp. For example, handles 113 may be semi- or half-circular in shape, instead of fully circular as depicted in FIG. 2, or may be shaped to conform to one or more fingers for comfortable use when grasped by a user. In other embodiments, handles 113 may simply be tabs that extend generally outward away from sheath member 101, which provide a surface for grasping with one or more fingers.

Holes 115 are depicted disposed proximate distal end 116 of sheath member 101. Holes 115 may have a sufficient diameter to allow for fluid to pass into lumen 117 of sheath member 101. For instance, in some embodiments, a sheet-like implant may be loaded onto implant spreader assembly 107, located within lumen 117 of sheath member 101, in a dry condition. Before using implant delivery system 100 to deploy the sheet-like implant to the target site, a user may submerge the distal end of sheath member 101 in a hydrating agent, which may pass into the interior of sheath member 101 through holes 115 and hydrate the sheet-like implant. In other instances, the target implant site may be inflated with one or more liquid agents in order to provide a greater working volume for maneuvering implant delivery system 100 at the target implant site. In such instances, the one or more liquid agents used to inflate the target implant site may act as hydrating agents for the sheet-like implant, for example by traversing holes 115 and contacting the sheet-like implant retained on implant spreader assembly 107.

Figure 3:
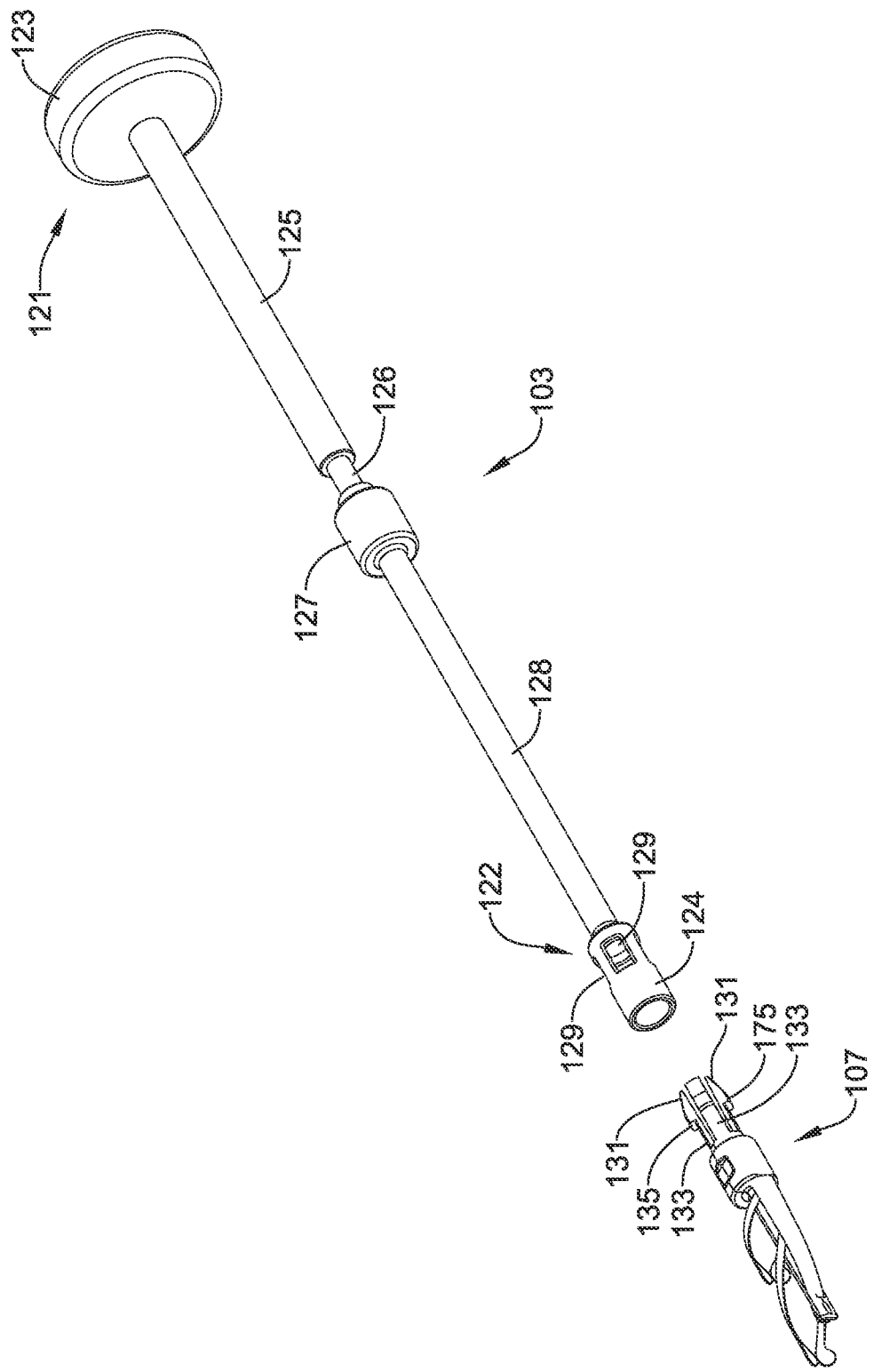
FIG. 3 is an exploded view of an exemplary implant delivery shaft and implant spreader assembly of the implant delivery system of FIG. 1, according to an example of the present disclosure.

FIG. 3 depicts implant delivery shaft 103 and implant spreader assembly 107 of implant delivery system 100 with sheath member 101 removed. Implant delivery shaft 103 has proximal end 121 and distal end 122. Additionally, implant delivery shaft 103 may be divided into different sections that have different diameters. For instance, implant delivery shaft 103 may have first section 125, second section 126, third section 127, and fourth section 128. First section 125 may have a first diameter, second section 126 may have a second diameter, third section 127 may have a third diameter, and fourth section 128 may have a fourth diameter. In at least some embodiments, all of the diameters may be different. For example, the second diameter may be less than the first diameter, and the third diameter may be greater than the first diameter. However, in some other embodiments, the fourth diameter may be the same as the first diameter. Although, in still other embodiments, the fourth diameter may be greater than, or less than, the first diameter.

In still other embodiments, implant delivery shaft 103 may have fewer than four sections. For instance, in some embodiments, implant delivery shaft 103 may have a first section, a second section, and a third section. In some of these embodiments, each section may have differing diameters, and in other embodiments, the first section and the third section, which may be separated by the second section, have the same diameter. In these embodiments, the second section may then have a smaller diameter. In other embodiments, however, the third section may have a larger or smaller diameter than the first section. In general, these are just example configurations of implant delivery shaft 103. The present disclosure contemplates variations of implant delivery shaft having any number of sections with any number of different diameters and wherein each section has a different or similar diameter than any other section in all variations.

As will be described in more detail below, the different diameters of implant delivery shaft 103 may, in conjunction with other members of implant delivery system 100, operate to prevent movement of implant delivery shaft 103 relative to sheath member 101.

Generally, the third diameter of third section 127 is less than the diameter of lumen 117, thereby allowing implant delivery shaft 103 to fit within sheath member 101. In at least some embodiments, third section 127 may additionally include a sealing member (not shown) disposed on third section 127. For instance, the sealing member may be a rubber or silicone o-ring like member disposed around third section 127. As described, in some instances one or more liquid agents may be pumped into the target implant site under pressure in order to inflate the target implant site. In embodiments where the sealing member is included, the sealing member may operate to prevent the one or more liquid agents from traversing distally, or proximally, of the sealing member. For instance, the sealing member may prevent the one or more liquid agents from traversing from the target implant site, up through lumen 117 of sheath member 101, and out the proximal end of implant delivery system 100 (and out of the patient). In other embodiments, the sealing member may comprise a coating that is applied to the surface of third section 127 in order to create a seal between the inside of sheath member 101 and third section 127. In other embodiments, the sealing member may be disposed on one of the other sections of implant delivery shaft 103. Implant delivery shaft 103 may include multiple sealing members located on different sections of implant delivery shaft 103.

Implant delivery shaft 103 may additionally comprise pushing member 123 attached to proximal end 121. Although shown as a generally circular component, in other embodiments, pushing member 123 may have any of a number of other suitable shapes. In general, pushing member 123 may have a diameter that is greater than that of any of sections 125, 126, 127, or 128 of implant delivery shaft 103. The greater diameter of pushing member 123 may provide a greater surface area for a user to apply pushing forces to implant delivery shaft 103. Additionally, in embodiments where the diameter of pushing member 123 is greater than the opening at proximal end 114 of sheath member 101, a user may only be able to advance implant delivery shaft 103 in the distal direction until pushing member 123 contacts flange 119 of sheath member 101.

In some embodiments, implant delivery shaft 103 may additionally include receiving member 124 attached to distal end 122 of implant delivery shaft 103. Although shown as having a diameter larger than fourth section 128 of implant delivery shaft 103, in other embodiments, receiving member 124 may have a smaller diameter, or a substantially similar diameter, to fourth section 128. Receiving member 124 may define a cavity for receiving implant spreader assembly 107. For instance, receiving member 124 may define an opening at the distal end of receiving member 124. In at least some embodiments, receiving member 124 may additionally include windows 129.

FIG. 3 additionally depicts implant spreader assembly 107, including retention members 131. Retention member 131 may include a flat portion 133 and a raised portion 135. Additionally, in some embodiments, each retention member 131 may taper as each retention member 131 extends proximally. This taper may make inserting implant spreader assembly 107 into receiving member 124 easier.

Figure 4:
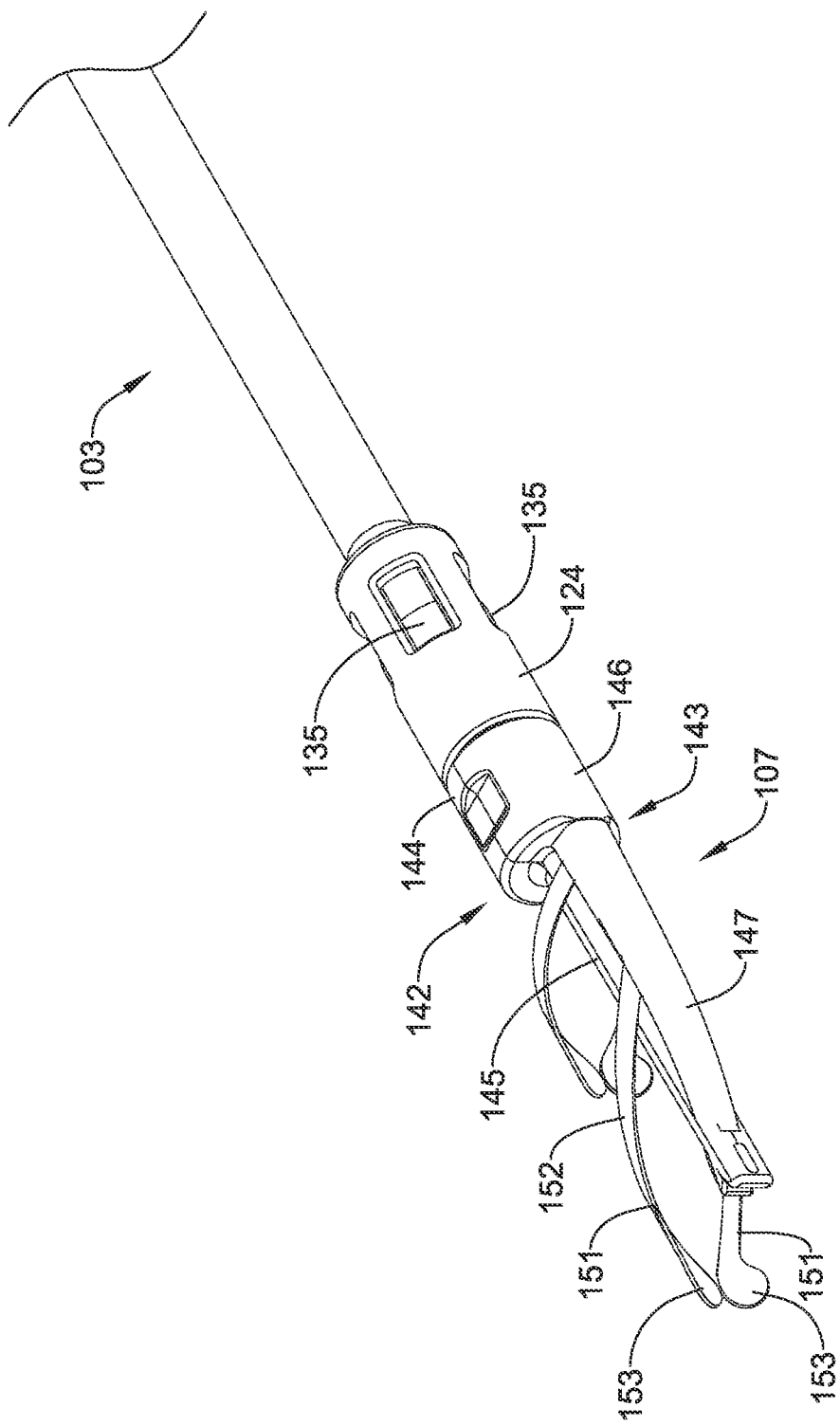
FIG. 4 is a perspective view of an exemplary implant delivery shaft and implant spreader assembly of the implant delivery system of FIG. 1, according to an example of the present disclosure.

When implant spreader assembly 107 is received within receiving member 124, retention members 131 of implant spreader assembly 107 may be disposed at least partially within windows 129 to retain implant spreader assembly 107 on implant delivery shaft 103, as shown in FIG. 4. More specifically, at least a portion of raised portions 135 may be disposed at least partially within windows 129, as shown in FIG. 4.

FIG. 4 additionally depicts other features of implant spreader assembly 107. For example, implant spreader assembly 107 may comprise first and second halves 142, 143. First half 142 may comprise body 144 and first post 145 extending generally distally away from body 144. Second half 143 may comprise body 146 and second post 147. In a similar manner to first post 145, second post 147 may also extend generally distally away from body 146. However, in contrast to first post 145, second post 147 may curve so that, when first half 142 and second half 143 are joined, second post 147 curves toward first post 145. When first half 142 and second half 143 are joined, first post 145 and second post 147 may define a slot with a narrow opening for receiving a sheet-like implant. For example, when retained on implant spreader assembly 107, a sheet-like implant may extend between first post 145 and second post 147. In other embodiments, implant spreader assembly 107 may comprise a single, unitary member, including first post 145 and second post 147.

Implant spreader assembly 107 may additionally include implant spreaders 151. As shown, each implant spreader 151 comprises an arm 152 ending in head 153. However, in other embodiments, implant spreaders 151 may have different shapes. For example, each implant spreader 151 may comprise multiple arms 152 and/end in multiple heads 153. Additionally, although FIG. 4 only depicts four implant spreaders 151, in other embodiments, implant spreader assembly 107 may include more or fewer implant spreaders 151.

In some embodiments, implant spreaders 151 may have a plurality of configurations. For instance, implant spreaders 151 may have a compact configuration, as shown in FIG. 4, where each arm 152 curves toward an opposing arm 152. Implant spreaders 151 may be disposed in this compact configuration, for example, when implant spreader assembly 107 is retained within lumen 117 of sheath member 101. When implant spreaders 151 are in an expanded configuration, each arm 152 may not curve and may instead extend in the same plane outward away from posts 145, 147. Implant spreaders 151 may be disposed in the expanded configuration, for example, when implant spreader assembly 107 is disposed outside lumen 117 of sheath member 101. Accordingly, when a sheet-like implant is retained on implant spreader assembly 107, the sheet-like implant may assume a curled or rolled configuration around implant spreaders 151, and may be constrained from unrolling when disposed within lumen 117 of sheath member 101 along with implant spreader assembly 107. However, once implant spreader assembly 107 is moved outside of lumen 117 of sheath member 101, implant spreaders 151 may assume their expanded configuration, thereby expanding or unfolding the sheet-like implant into a generally planar configuration.

Accordingly, in at least some embodiments, implant spreaders 151 may be made of a material that may deform elastically into one or more shapes in order to fit within the confines of sheath member 101. Some suitable example materials include metals and metal alloys including stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In at least some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some cases, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In other embodiments, implant spreaders 151 may be constructed of one or more of the above described materials configured as an inlay. For instance implant spreaders 151 may comprise a metal structure encased in one or more other materials, such as a plastic or silicone material. The plastic or silicone material may be molded either completely or partly over the metal structure. Such hybrid-material structures may reduce the manufacturing cost of producing implant spreaders 151 or provide implant spreaders 151 with physical properties unable to be achieved by using only metal.

Figure 5:
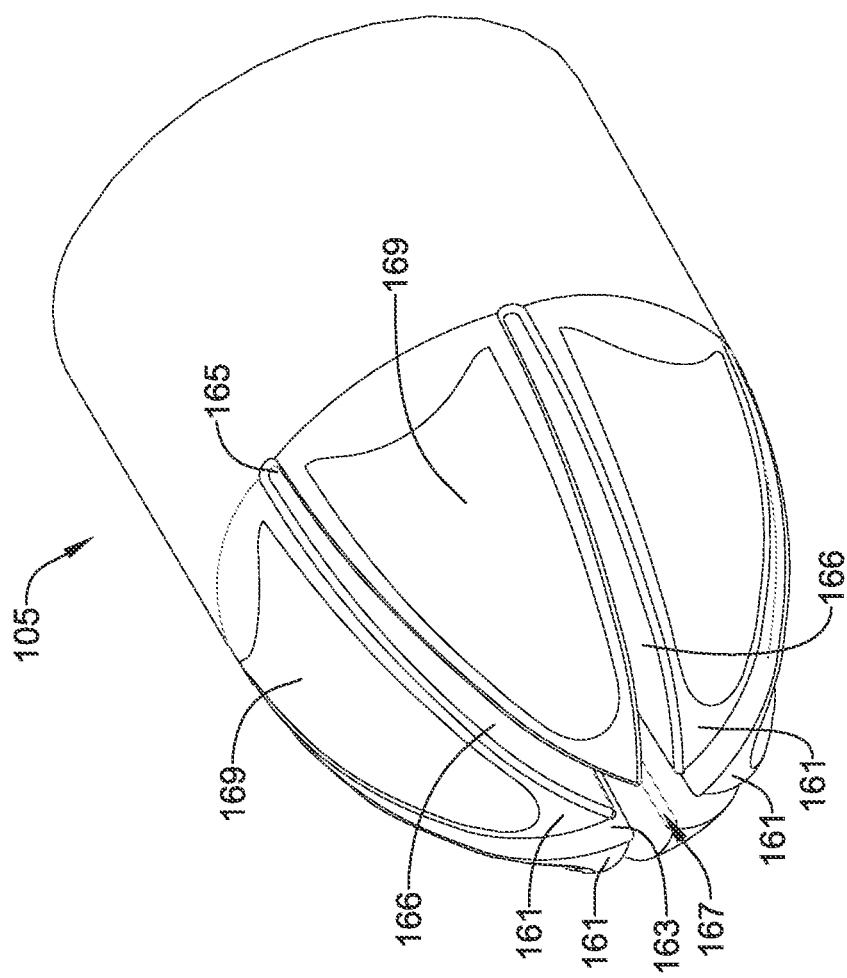
FIG. 5 is a perspective view of an exemplary cap of the implant delivery system of FIG. 1, according to an example of the present disclosure.

FIG. 5 is a perspective view of cap 105. In some embodiments, cap 105 may make it easier for a user to insert implant delivery system 100 into the patient, for example by allowing use of implant delivery system 100 without an obturator. For instance, cap 105 may help to keep tissue from entering lumen 117 of sheath member 101 as implant delivery system 100 is inserted into tissue through an incision in the patient. In some embodiments, cap 105 formed separately from sheath member 101 and may be attached to distal end 116 of sheath member 101 using one or more adhesives, by laser welding, with a friction fit, or any other suitable means for attachment. Forming cap 105 separate from sheath member 101 may allow for attachment of implant spreader assembly 107 to implant delivery shaft 103 after implant delivery shaft 103 has been inserted into lumen 117 of sheath member 101. However, in other embodiments, cap 105 may be formed integrally with sheath member 101 and implant spreader assembly 107 may be attached to implant delivery shaft 103 before implant delivery shaft 103 is loaded into sheath member 101.

In general, cap 105 may comprise a plurality of petals 161. Each petal 161 may curve inward toward central longitudinal axis 112 (as depicted in FIG. 2) and taper as each petal 161 extends distally, so as to create narrow opening 167. In at least some embodiments, cap 105 comprises an even number of petals 161. More specifically, in at least some embodiments, cap 105 comprises four, six, eight, ten, or any other suitable number of petals. However, in other embodiments, cap 105 may comprise an odd number of petals 161.

In examples where cap 105 comprises an even number of petals 161, as implant delivery system 100 is being inserted into an incision, opposite petals 161 may collapse against each other when being advanced through the incision and into tissue due to tissue pressing on cap 105, thereby substantially closing narrow opening 167. This may help prevent tissue from entering lumen 117 of sheath member 101. For instance, each petal 161 may have a thickness extending from an outer surface to an inner surface, forming face 166. The petal thickness may vary in different embodiments between about 0.05 inches (1.27 mm) and about 0.15 inches (3.81 mm). As a force is applied to the outer surface of petals 161 and petals 161 collapse together such that faces 166 of one petal 161 converge with adjacent faces 166 of adjacent petals 161, faces 166 may become pressed together. In this manner, each of petals 161 may support each other when a force is applied to the outer surface of petals 161. The thickness and configuration of petals 161 may help to prevent petals 161 from buckling inward at points between tips 163 and bases 165 when forces are applied to the outside surface of petals 161. With faces 166 pressed together (e.g. abutting one another), petals 161 may form a solid plug which prevents tissue from entering lumen 117 of sheath member 101 as implant delivery system 100 is advanced through tissue.

Additionally, when faces 166 are pressed together under a force acting on the outside surface of petals 161, petals 161 may translate such forces into a force acting in a substantially axial direction at bases 165, for instance along central longitudinal axis 112. In at least some embodiments, bases 165 may be relatively flexible in directions perpendicular to the central longitudinal axis 112, but may be inflexible in directions along central longitudinal axis 112. For example, petals 161 may taper in thickness from tips 163 to bases 165. This configuration may create a hinge-like connection between petals 161 and the rest of cap 105.

As discussed, when a force is applied to the outer surface of petals 161, petals 161 are configured to collapse together. However, when a force is applied to an inner surface of petals 161 (e.g., from an interior of the cap 105, the force pushes petals 161 in an outward direction away from each other. If the force is large enough, petals 161 will bend at bases 165 and diverge from one another, exposing lumen 117 of sheath member 101. For example, when implant delivery system 100 is positioned at an implant location, a user may advance implant delivery shaft 103 distally relative to sheath member 101. As the user advances implant spreader assembly 107 distally, implant spreader assembly 107 may push against the inside surface of petals 161. This pushing force may cause each petal 161 to bend outward at or near base 165, thereby causing tips 163 to expand outward way from central longitudinal axis 112 and causing narrow opening 167 to expand to allow implant spreader assembly 107 to be advanced distally beyond petals 161.

In some additional embodiments, as depicted in FIG. 5, each petal 161 may have a recessed portion 169. Recessed portions 169 may allow petals 161 to be formed from less overall material and/or may help in reducing the thickness of petals 161 at tips 163 and at bases 165, thereby increasing the flexibility of petals 161 at bases 165 relative to tips 163. In still additional embodiments, faces 166 may include a series of interlocking protrusions and grooves. The protrusions on a first petal 161 may be aligned with grooves on a second, adjacent petal 161 such that when faces 166 are compressed together, the protrusions of the first petal 161 extend into the grooves on the second petal 161. These series of protrusions and grooves may help to prevent petals 161 from slipping past one another or otherwise deviating from a tight, compressed configuration when a force is applied to the outer surface of petals 161.

Figure 6:
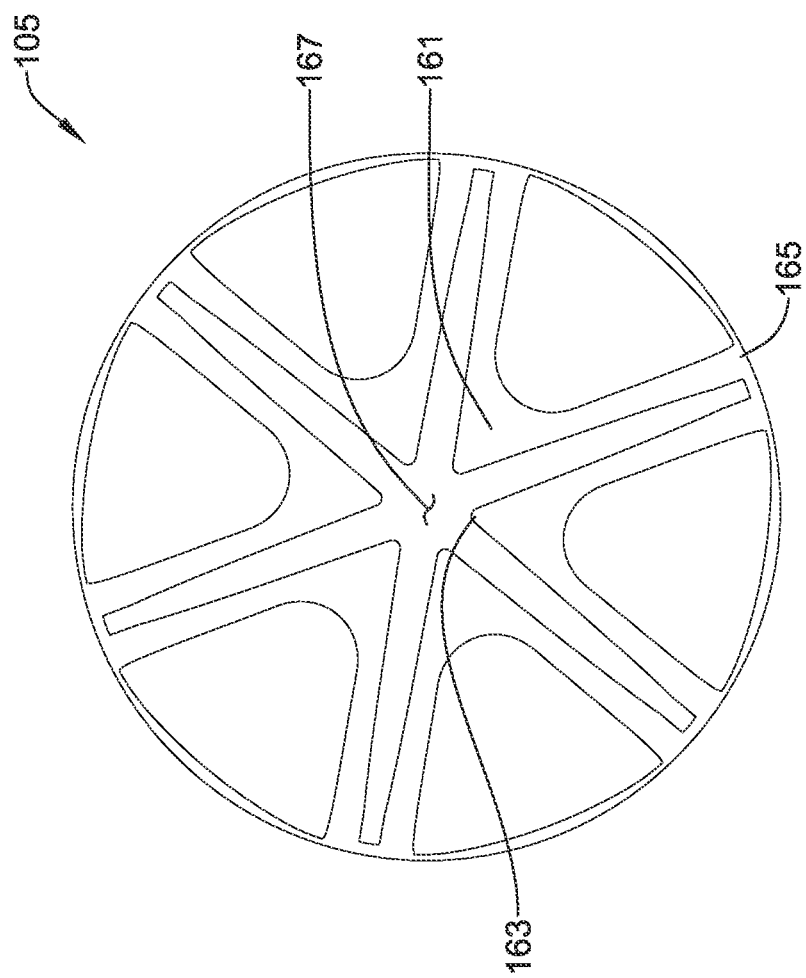
FIG. 6 is a front plan view of the cap of FIG. 5.

FIG. 6 is a front-plan view of cap 105, more closely detailing narrow opening 167. In different embodiments, the gap between opposing tips 163 of petals 161 may be between about 0.010 inches (0.254 mm) and about 0.025 inches (0.635 mm). Additionally, this gap between petals 161 at tips 163 may narrow toward bases 165 of petals 161. For instance, the gap may narrow to between about 0.006 inches (0.152 mm) and about 0.015 inches (0.381 mm) at bases 165 of petals 161. Gaps of these sizes may allow cap 105 to be manufactured using injection molding techniques that would be unavailable if petals 161 were formed with no gaps between petals 161. In some instances, cap 105 may be molded as a solid piece, and then undergo a secondary operation to form gaps to define petals 161, such as using a laser or razor, for example.

However, in other embodiments, cap 105 may not have narrow opening 167. Rather, cap 105 may have no opening. For instance, petals 161 may be formed so that petals 161 are pressed together to completely seal off lumen 117 of sheath member 101. In some of these embodiments, slits may be formed between petals 161 to weaken a bond between petals 161 such that a force acting on petals 161 from inside sheath member 101, such as by implant spreader assembly 107, petals 161 may expand apart from one another exposing the lumen of sheath member 101. In other embodiments, cap 105 may include narrow opening 167, but a thin membrane-like member (not shown) may be placed over petals 161. The membrane-like member may be made from one or more various plastic, silicone, rubber, or other suitable materials. The membrane-like member may help prevent tissue from entering lumen 117 of sheath member 101 when implant delivery system 100 is inserted into a patient. However, the membrane-like member may be fragile enough such that the membrane-like member breaks or tears when a user advances implant delivery shaft 103 distally, causing petals 161 to bend outward expanding narrow opening 167.

Figure 7:
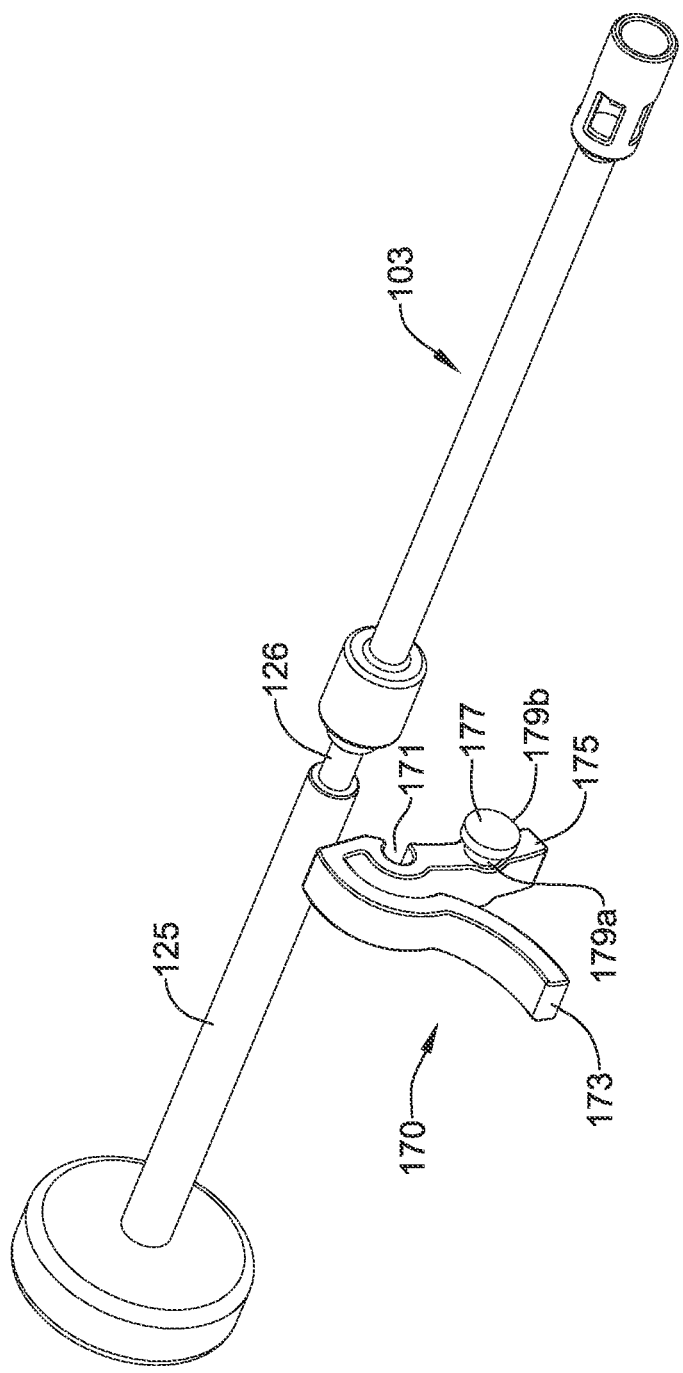
FIG. 7 is an exploded view of the implant delivery shaft of FIG. 4 and an exemplary distal movement lock, according to an example of the present disclosure.

FIG. 7 depicts distal movement lock 170 along with implant delivery shaft 103. Distal movement lock 170, when engaged with implant delivery shaft 103, may prevent implant delivery shaft 103 from being advanced distally. For instance, distal movement lock 170 may comprise first handle 173, second handle 175, and opening 171. When distal movement lock 170 is engaged with implant delivery shaft 103, opening 171 may be engaged with second section 126. For instance, the diameter of opening 171 may be slightly smaller than the second diameter of second section 126 such that, when distal movement lock 170 is engaged with implant delivery shaft 103, distal movement lock 170 grips second section 126. Additionally, the diameter of opening 171 in the unstressed state may have a diameter that is less than the first diameter of first section 125. Accordingly, when engaged with implant delivery shaft 103, the smaller diameter of opening 171 may prevent implant delivery shaft 103 from being advanced distally.

Once a user has positioned implant delivery system 100 at the target implant site and is ready to deploy the sheet-like implant, the user may squeeze together first handle 173 and second handle 175. This action may transition distal movement lock 170 into a stressed state and may act to increase the diameter of opening 171. In this stressed state, distal movement lock 170 may be easily removed from around second section 126, thereby allowing the user to advance implant delivery shaft 103 distally.

In some embodiments, distal movement lock 170 may additionally include retention member 177. In some embodiments, retention member 177 may comprise narrow portion 179a and wide portion 179b. In such embodiments, retention member 177 may engage with another member of implant delivery system 100, and allow for rotational movement of distal movement lock 170 relative to the other member of implant delivery system 100. In such embodiments, after the user has squeezed handles 173 and 175 together, distal movement lock 170 may be rotated away from implant delivery shaft 103.

Figure 8:
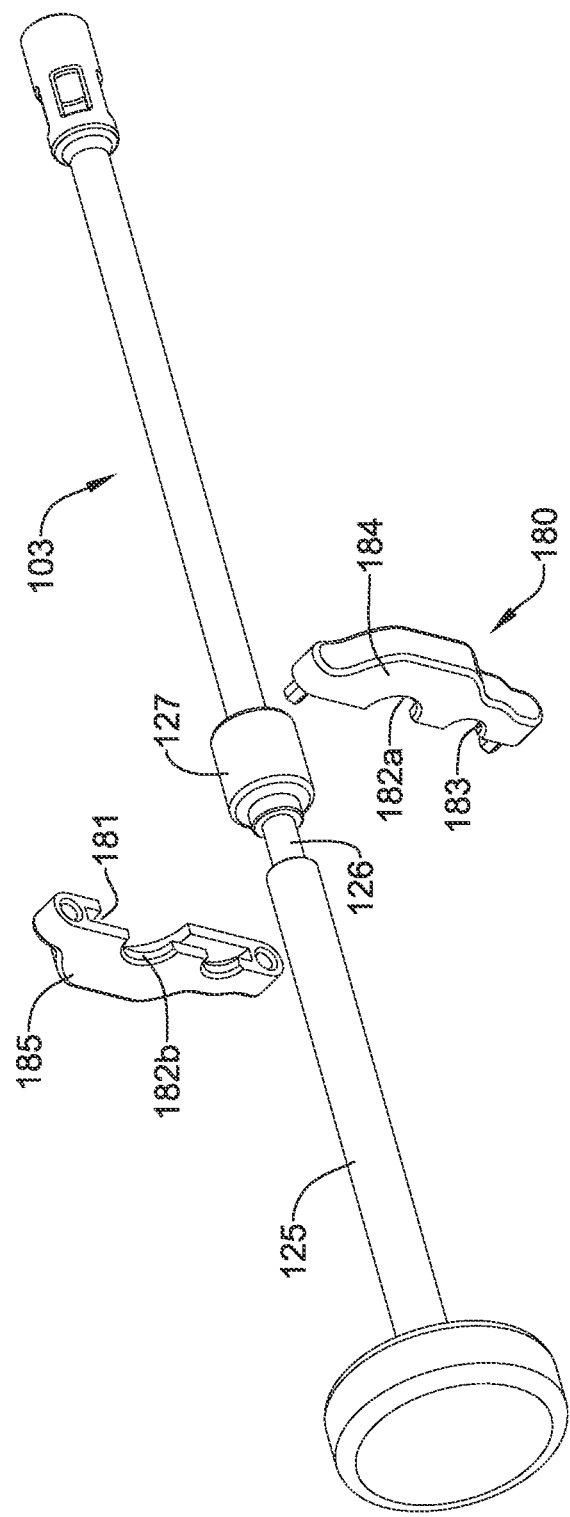
FIG. 8 is an exploded view of the implant delivery shaft of FIG. 4 and an exemplary proximal movement lock, according to an example of the present disclosure.

FIG. 8 depicts proximal movement lock 180. In some embodiments, proximal movement lock 180 may be comprised of two sections, first section 184 and second section 185. When connected together, first section 184 and second section 185 may form one or more openings. For instance, as depicted in FIG. 8, first section 184 of proximal movement lock 180 defines a number of openings, opening 182a and opening 183. Second section 185 additionally defines slot 185. Although not explicitly shown in the perspective view in FIG. 8, in general, each of first section 184 and second section 185 may define one portion of an opening or slot that, when halves 184, 185 are put together, define an entire opening or slot.

For instance, when halves 184, 185 are put together, opening 182a and 182b come together to form a single opening. The opening formed by opening 182a and 182b may have a diameter that is smaller than the third diameter of third section 127. Accordingly, when implant delivery system 100 is fully assembled and proximal movement lock 180 is in place, the opening formed by opening 182a and 182b only allows implant delivery shaft 103 to be advanced proximally until third section 127 contacts proximal movement lock 180.

In a similar manner, when halves 184, 185 are put together, halves 184, 185 form slot 181. Slot 181 may be sized to fit around flange 119 of sheath member 101. Accordingly, to attach proximal movement lock 180 to sheath member 101, halves 184, 185 may be connected together around flange 119 such that flange 119 resides within slot 181 to secure proximal movement lock 180 to sheath member 101.

In some embodiments, when halves 184, 185 are put together, halves 184, 185 may additionally form opening 183. In these embodiments, opening 183 may be sized to receive retention member 177 of distal movement lock 170. For instance, narrow portion 179a may fit through opening 183, while wide portion 179b does not. Accordingly, if halves 184, 185 are connected together with opening 183 around narrow portion 179a, wide portion 179b of retention member 177 may retain distal movement lock 170 with proximal movement lock 180. In such a configuration, retention member 177 may still allow for rotational movement between distal movement lock 170 and proximal movement lock 180.

Although shown in FIGS. 1, 7, and 8, and described in conjunction with implant delivery system 100 above, some embodiments of implant delivery system 100 may not include distal movement lock 170 and/or proximal movement lock 180. In other embodiments, implant delivery system 100 may only include a single locking member that prevents both proximal and distal movement of implant delivery shaft 103 until the single locking member is opened.

Figure 9:
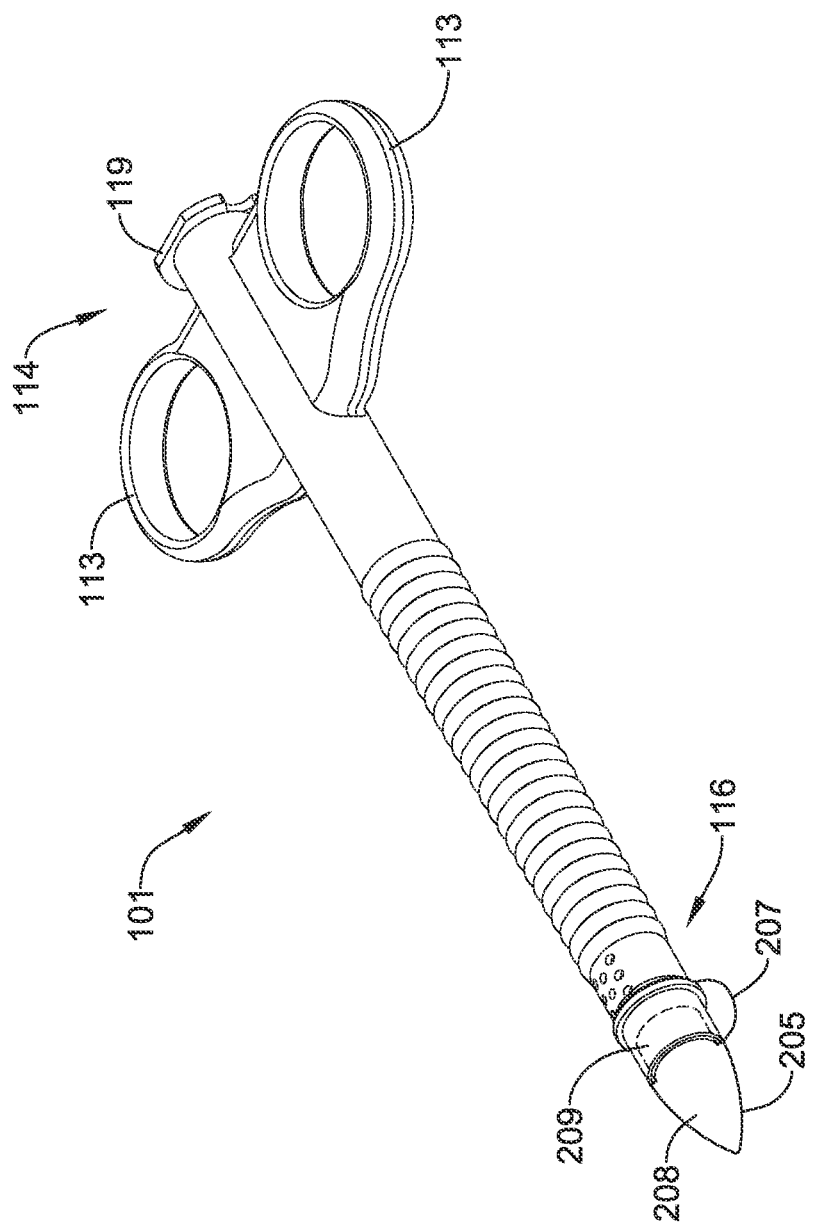
FIGS. 9 and 10 are perspective views of an alternative exemplary cap, according to an example of the present disclosure.
Figure 10:
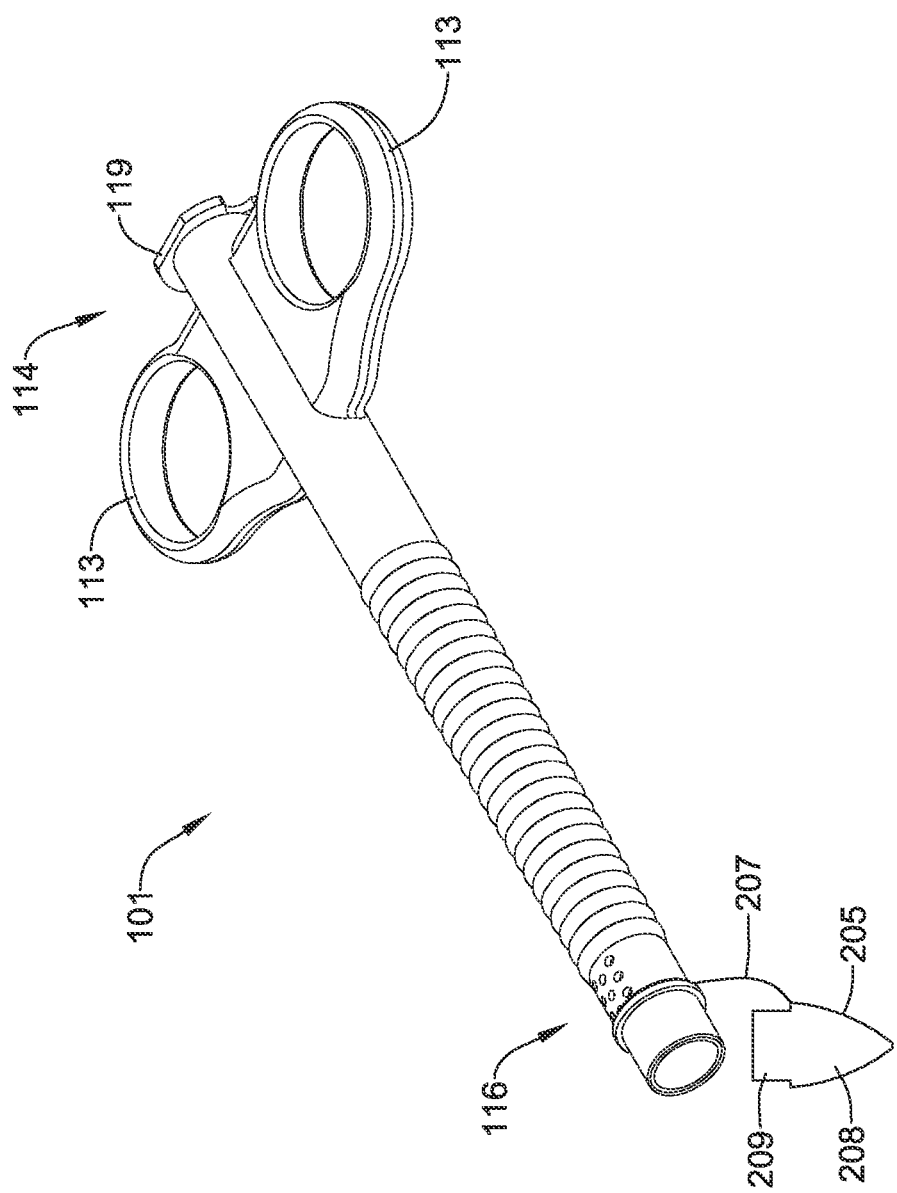

FIGS. 9 and 10 depict an alternative embodiment of implant delivery system 100 including an alternate cap 205. For example, FIG. 9 depicts sheath member 101 including cap 205. In these embodiments, cap 205 may be a plug that fits at least partially within lumen 117 of sheath member 101. For example, cap 205 may have a base portion 209 and a top portion 208. Base portion 209 may be generally circular in diameter to conform to the inner wall of sheath member 101 when base portion 209 resides within lumen 117. Top portion 208 may have a taper as cap 205 extends in the distal direction to aid with insertion into an incision. When base portion 209 is inserted within sheath member 101, there may not be a gap between the walls of sheath member 101 defining lumen 117 and base portion 209. In this manner, when cap 205 is inserted into sheath member 101, cap 205 may prevent tissue from entering lumen 117 when implant delivery system 100 is inserted into an incision in a patient.

Cap 205 may be additionally attached to sheath member 101 by tether 207. Tether 207 may be a piece of string, or wire, or any other suitable flexible material. Once implant delivery system 100 has been maneuvered to the target implant site, a user may advance implant delivery shaft 103 distally. As this happens, implant spreader assembly 107 may push against base portion 209 and may push cap 205 out of lumen 117, as depicted in FIG. 10. Once cap 205 has been pushed out of lumen 117, implant spreader assembly 107 may be pushed, through additional distal advancement of implant delivery shaft 103, distally past the opening at distal end 116 of sheath member 101. Tether 207 may keep cap 205 attached to sheath member 101 so that, as implant delivery system 100 is retracted from within the patient, cap 205 is also retracted.

Figure 11:
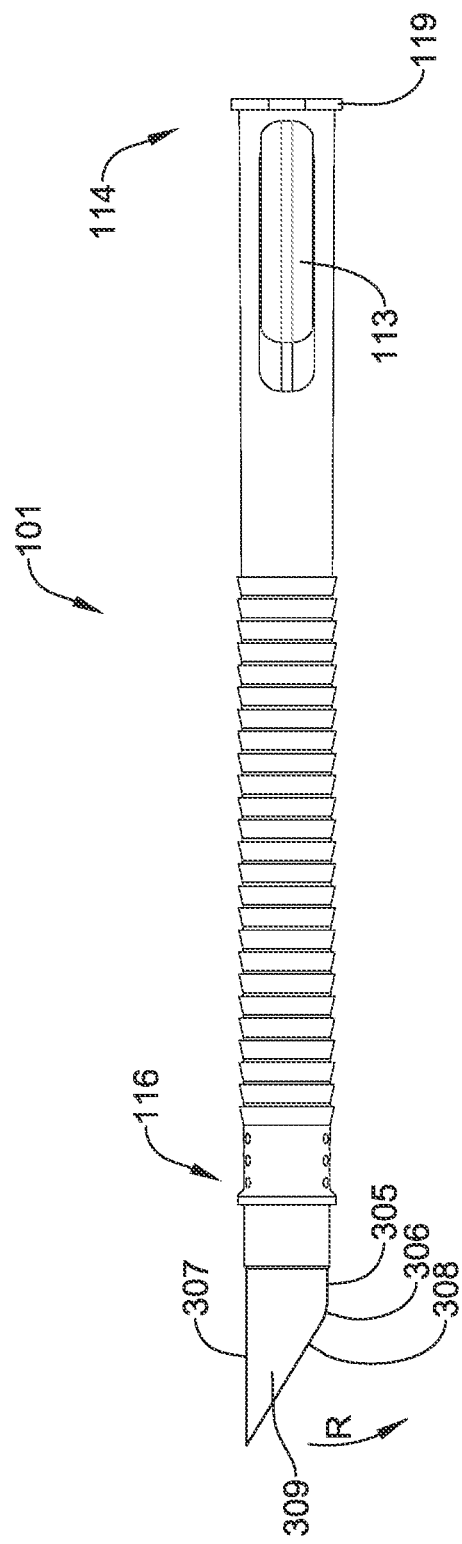
FIGS. 11 and 12 are perspective views of another alternative exemplary cap, according to an example of the present disclosure.
Figure 12:
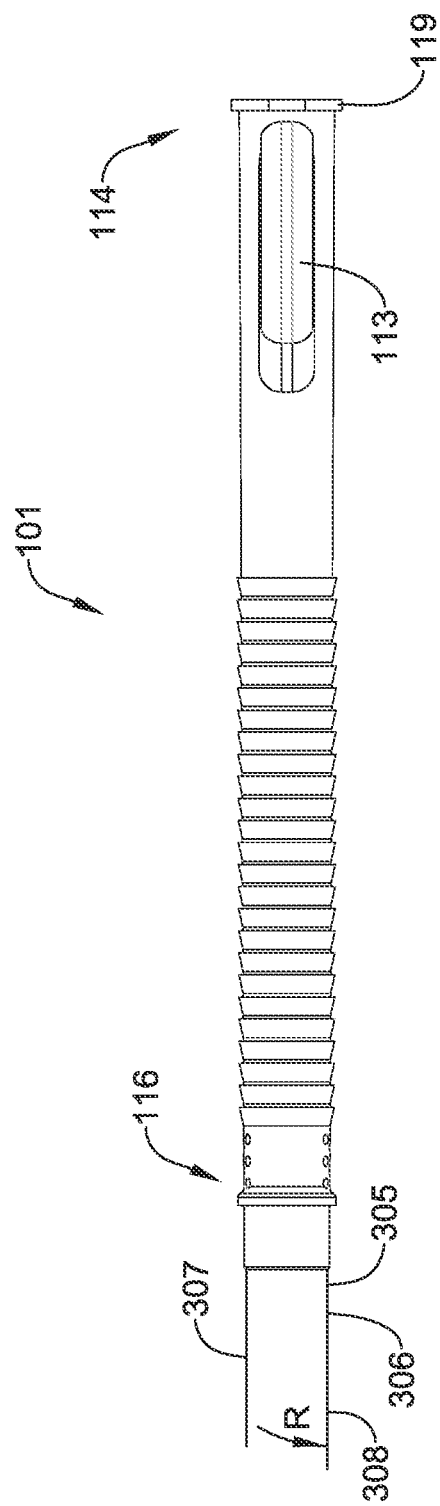

FIGS. 11 and 12 depict another alternative embodiment of implant delivery system 100 including an alternate cap 305. For example, FIG. 11 depicts sheath member 101 including cap 305. In these embodiments, cap 305 may comprise base portion 307 and flap or lid member 309. Lid member 309 may be hollow and have a generally smooth, rounded outer surface and may taper as cap 305 extends distally. Lid member 309 may also include hinged flap 308 that connected to the rest of lid member 309 by hinge 306.

In some embodiments, base portion 307 may be generally flat and extend from distal end 116 of sheath member 101. When in a closed position, lid member 309, including hinged flap 308, may fit together with base portion 307 to seal off lumen 117 of sheath member 101. Accordingly, when implant delivery system 100 is inserted into a patient, lid member 309 may prevent tissue from entering lumen 117. When implant delivery system 100 has been positioned at the target implant site, the user may advance implant delivery shaft 103 distally. This movement may cause implant spreader assembly 107 push against the inside of lid member 309, and in particular the inside of hinged flap 308. This force against hinged flap 308 may cause hinged flap 308 to rotate about hinge 306, for instance in the direction of arrow R, exposing the lumen 117 of sheath member 101, as shown in FIG. 12. Implant spreader assembly 107 may then be advanced distally beyond cap 305 to a target site and deployed. Implant spreader assembly 107 may then be retracted back into lumen 117 of sheath 101 and implant delivery system may be withdrawn from the patient.

In still other embodiments similar to FIGS. 11 and 12, instead of base portion 307 being a part of cap 305, a portion of sheath member 101 may extend distally beyond distal end 116 and act as base portion 307. For instance, cap 305 may only be comprised of lid member 309 which would fit together with the extension of sheath member 101 to seal off lumen 117.

Figure 13:
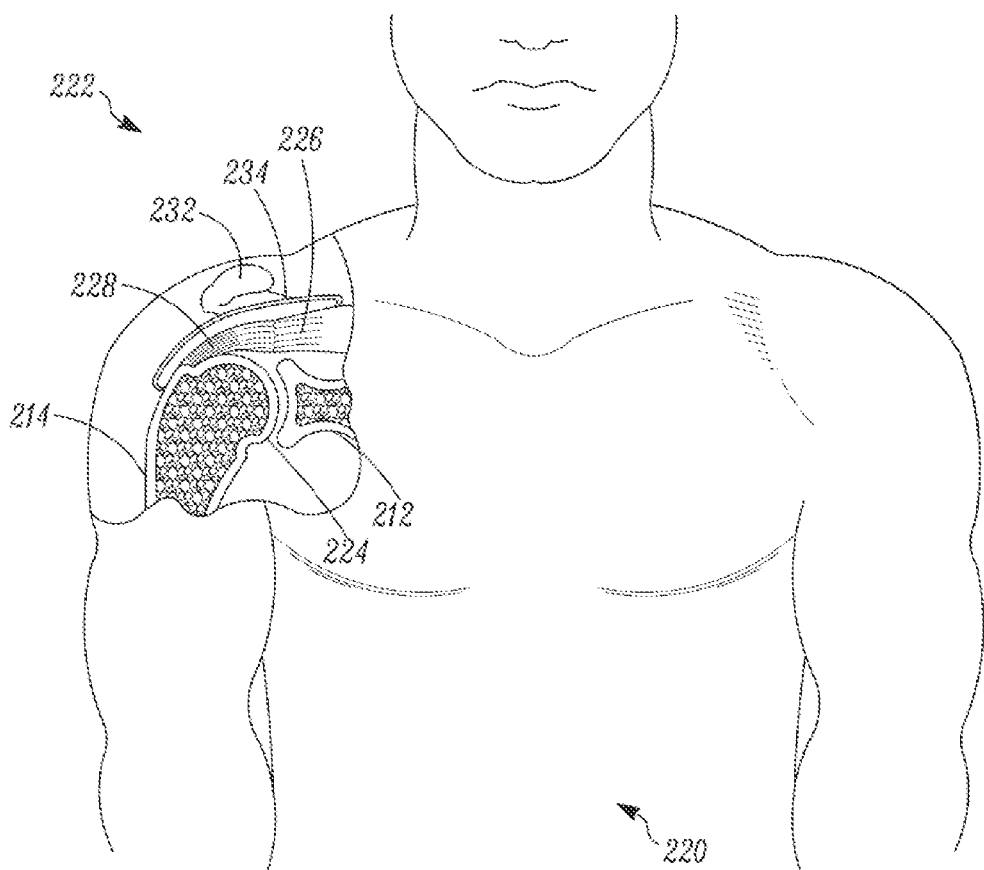
FIG. 13 is a stylized anterior view of a patient with a shoulder being shown in cross-section, according to an example of the present disclosure.

FIG. 13-16B illustrate an exemplary use or application of implant delivery system 100. FIG. 13 is a stylized anterior view of patient 220. For purposes of illustration, shoulder 222 of patient 220 is shown in cross-section in FIG. 13. Shoulder 222 includes humerus 214 and scapula 212. In FIG. 13, head 224 of humerus 214 can be seen mating with a glenoid fossa of scapula 212 at a glenohumeral joint. The glenoid fossa comprises a shallow depression in scapula 212. The movement of humerus 214 relative to scapula 212 is controlled by a number of muscles including: the deltoid, the supraspinatus, the infraspinatus, the subscapularis, and the teres minor. For purposes of illustration, only supraspinatus 226 is shown in FIG. 13.

With reference to FIG. 13, distal tendon 228 of supraspinatus 226 meets humerus 214 at an insertion point. Scapula 212 of shoulder 222 includes acromion 232. Subacromial bursa 234 is shown extending between acromion 232 of scapula 212 and head 224 of humerus 214. Subacromial bursa 234 is shown overlaying supraspinatus 226 as well as supraspinatus tendon 228 and a portion of humerus 214. Subacromial bursa 234 is one of the hundreds of bursae found the human body. Each bursa comprises a fluid filled sac. The presence of these bursae in the body reduces friction between bodily tissues.

Exemplary implant delivery system 100 described herein may be used to position and deploy a sheet-like implant to various target tissues throughout the body. The shoulder depicted in FIG. 13 is one example where the sheet-like implant may be affixed to one or more bones associated with an articulating joint, such as the glenohumeral joint. Additionally, the sheet-like implant may be affixed to one or more tendons to be treated. The tendons to be treated may be torn, partially torn, have internal micro-tears, be untorn, and/or be thinned due to age, injury or overuse. Implantation of the sheet-like implant at such locations may provide beneficial therapeutic effect on a patient experiencing joint pain believed to be caused by partial thickness tears and/or internal microtears. In some cases, applying the sheet-like implant early before a full tear or other injury develops may cause the tendon to thicken and/or at least partially repair itself, thereby avoiding more extensive joint damage, pain, and the need for more extensive joint repair surgery.

Figure 14:
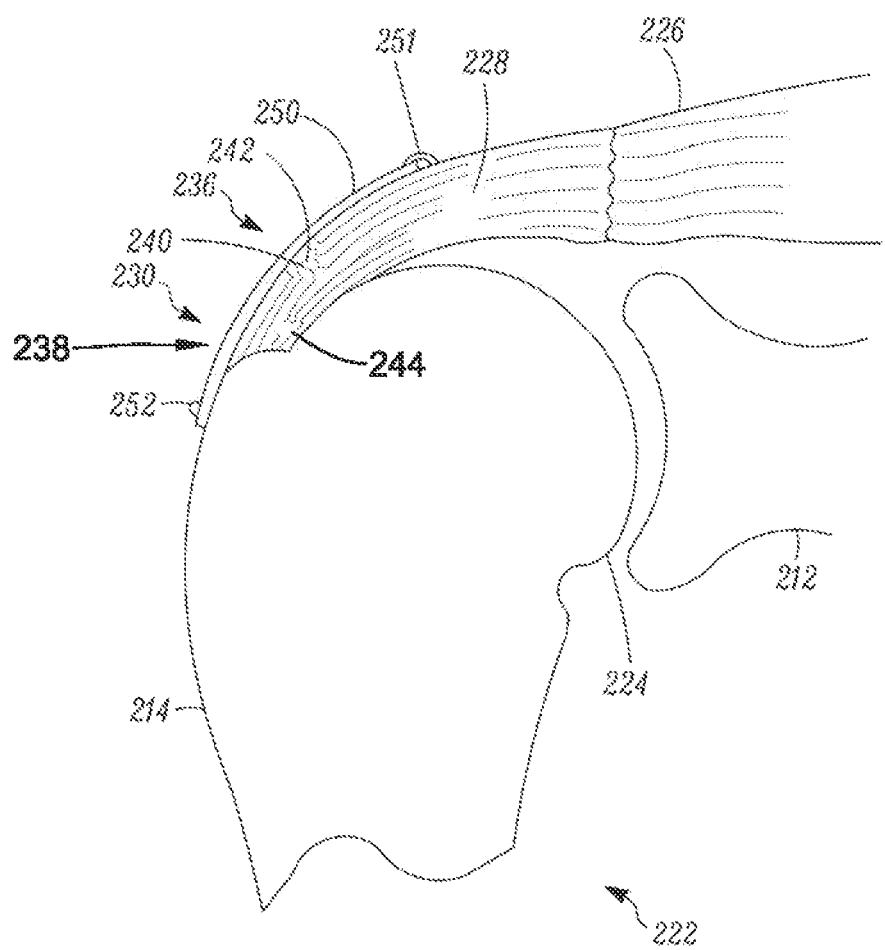
FIG. 14 is a stylized view of a shoulder depicting a head of the humerus shown mating with the glenoid fossa of the scapula at a glenohumeral joint and an implant affixed to a tendon, according to an according to an example of the present disclosure.

FIG. 14 is a stylized anterior view of shoulder 222 including humerus 214 and scapula 212. In FIG. 14, head 224 of humerus 214 is shown mating with a glenoid fossa of scapula 212 at a glenohumeral joint. Supraspinatus 226 is also shown in FIG. 14. This muscle, along with others, controls the movement of humerus 214 relative to scapula 212. Distal tendon 228 of supraspinatus 226 meets humerus 214 at insertion point 230.

As depicted in FIG. 14, distal tendon 228 includes first damaged portion 236. A number of loose tendon fibers 240 in first damaged portion 236 are visible in FIG. 14. First damaged portion 236 includes first tear 242 extending partially through distal tendon 228. First tear 242 may therefore be referred to as a partial thickness tear. With reference to FIG. 14, first tear 242 begins on the side of distal tendon 228 facing the subacromial bursa (shown FIG. 13) and ends midway through distal tendon 228. Accordingly, first tear 242 may be referred to as a bursal side tear.

With reference to FIG. 14, distal tendon 228 includes second damaged portion 238 located near insertion point 230. As illustrated, second damaged portion 238 of distal tendon 228 has become frayed and a number of loose tendon fibers 240 are visible. Second damaged portion 238 of distal tendon 228 includes second tear 244. Second tear 244 begins on the side of distal tendon 228 facing the center of the humeral head 224. Accordingly, second damaged portion 238 may be referred to as an articular side tear.

FIG. 14 illustrates sheet-like implant 250, which has been placed over the bursal side of distal tendon 228. Sheet-like implant 250 is affixed to distal tendon 228 by a plurality of tendon staples 251. In some examples, sheet-like implant 250 may comprise one or multiple of a number of different materials without deviating from the spirit and scope of the present disclosure. In some examples, sheet-like implant 250 may comprise a plurality of fibers. The fibers may be interlinked with one another. When this is the case, sheet-like implant 250 may comprise a plurality of apertures comprising the interstitial spaces between fibers. Various processes may be used to interlink the fibers with one another. Examples of processes that may be suitable in some applications including weaving, knitting, and braiding. In some embodiments, sheet-like implant 250 may comprise a laminate including multiple layers of film with each layer of film defining a plurality of micro-machined or formed holes. Sheet-like implant 250 may also comprise a reconstituted collagen material having a porous structure. Additionally, sheet-like implant 250 may also comprise a plurality of electro-spun nanofiber filaments forming a composite sheet. Additionally, sheet-like implant 250 may comprise a synthetic sponge material that defines a plurality of pores. Sheet-like implant 250 may also comprise a reticulated foam material. Reticulated foam materials that may be suitable in some applications are available from Biomerix Corporation of Fremont, California which identifies these materials using the trademark BIOMERIX BIOMATERIAL™. Sheet-like implant 250 may be circular, oval, oblong, square, rectangular, or other shape configured to suit the target anatomy.

Sheet-like implant 250 is affixed to humerus 214 by a plurality of bone staples 252. Sheet-like implant 250 extends over insertion point 230, first tear 242 and second tear 244. In other cases, sheet-like implant 250 may be placed on the bursal side of a tendon regardless of whether the tears being treated are on the bursal side, articular side or within the tendon. In some cases the exact location and nature of the tears being treated may be unknown. Sheet-like implant 250 may be applied to the bursal side of a tendon to treat shoulder pain that is most likely caused by one or more partial thickness tears in the tendon.

Figure 15A:
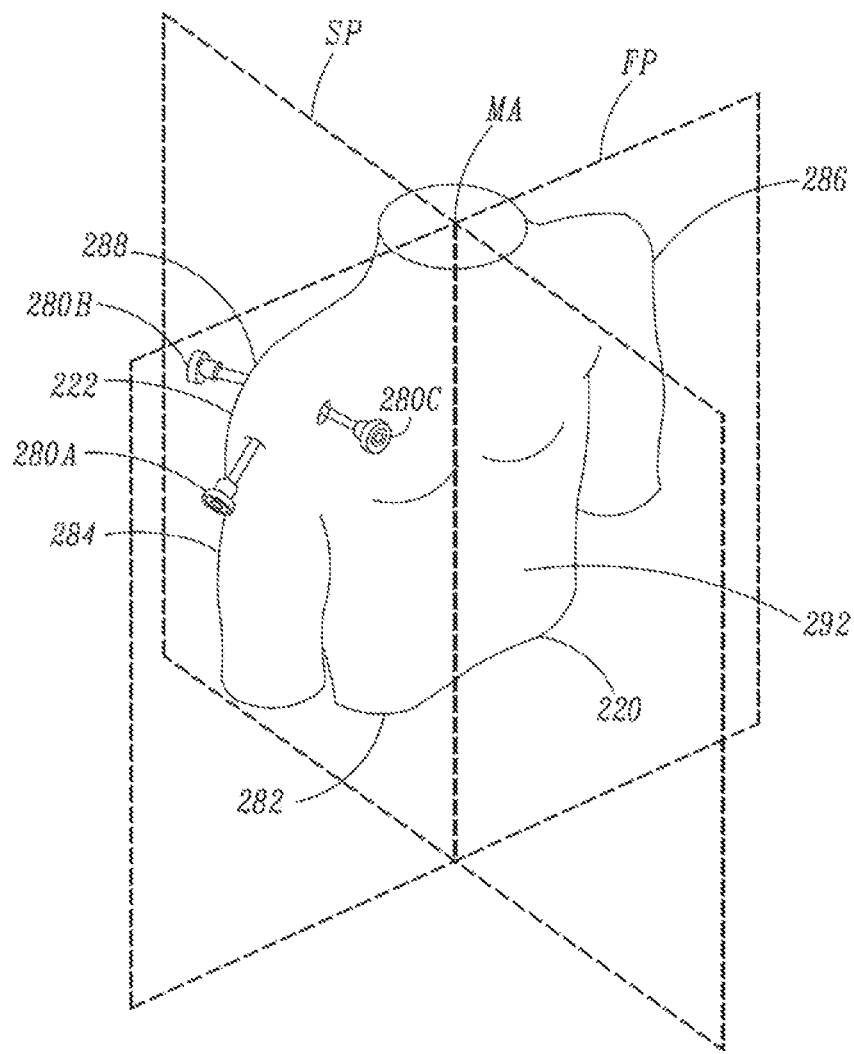
FIG. 15A is a stylized perspective view showing a portion of the body of a human patient divided into quadrants by planes, according to an example of the present disclosure.

FIG. 15A is a stylized perspective view showing a portion of body 282 of human patient 220. Body 282 includes shoulder 222. In the exemplary embodiment of FIG. 15A, a plurality of cannulas are positioned to access a treatment site within shoulder 222. In some cases, shoulder 222 may be inflated by pumping a continuous flow of saline through shoulder 222 to create a cavity proximate the treatment site. The cannulas shown in FIG. 15A include first cannula 280A, second cannula 280B and third cannula 280C.

In FIG. 15A, a sagital plane SP and a frontal plane FP are shown intersecting body 282. Sagital plane SP and frontal plane FP intersect one another at a medial axis MA of body 282. With reference to FIG. 15A, sagital plane SP bisects body 282 into a right side 284 and a left side 286. Also with reference to FIG. 15A, frontal plane FP divides body 282 into an anterior portion 292 and a posterior portion 288. Sagital plane SP and a frontal plane FP are generally perpendicular to one another. These planes and portions are used to describe the procedures used in exemplary embodiments.

First cannula 280A is accessing a treatment site within shoulder 222 using a lateral approach in which first cannula 280A pierces the outer surface of right side 284 of body 282. The term lateral approach could also be used to describe situations in which an instrument pierces the outer surface of left side 286 of body 282. Second cannula 280B is accessing a treatment site within shoulder 222 using a posterior approach in which second cannula 280B pierces the outer surface of posterior portion 288 of body 282. Third cannula 280C is accessing a treatment site within shoulder 222 using an anterior approach in which third cannula 280C pierces the outer surface of anterior portion 292 of body 282.

Figure 15B:
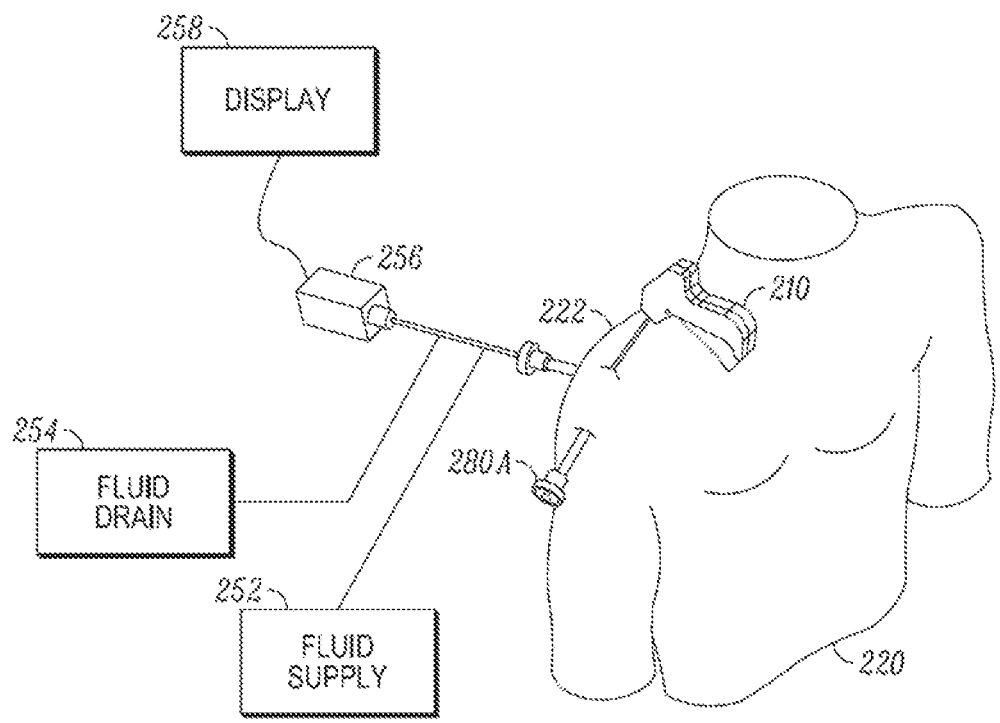
FIG. 15B is a stylized perspective view illustrating an exemplary procedure for arthroscopic treatment of a shoulder of a patient, according to an example of the present disclosure.

FIG. 15B is a stylized perspective view illustrating an exemplary procedure for treating a shoulder 222 of a patient 220 using implant device system 100. The procedure illustrated in FIG. 15B may include, for example, fixing tendon repair implants to one or more tendons of shoulder 222. The tendons treated may be torn, partially torn, have internal micro-tears, be untorn, and/or be thinned due to age, injury or overuse.

Shoulder 222 of FIG. 15B has been inflated to create a cavity therein. A fluid supply 252 is pumping a continuous flow of saline into the cavity. This flow of saline exits the cavity via a fluid drain 254. A camera 256 provides images from inside the cavity. The images provided by camera 256 may be viewed on a display 258. Camera 256 may be used to visually inspect the tendons of shoulder 222 for damage. In some cases, sheet-like implant 250 may be affixed to a bursal surface of the tendon regardless of whether there are visible signs of tendon damage.

Implant delivery system 100 may, for example, be inserted into shoulder 222 through first cannula 280A. In certain embodiments, first cannula 280A can access a treatment site within shoulder 222 using a lateral approach in which first cannula 280A pierces the outer surface of a right side of the patient's body. In some cases a physician may choose not to use a cannula in conjunction with implant delivery system 100. When that is the case, the implant delivery system 100 may be advanced through tissue.

Once implant delivery system 100 has been positioned within shoulder 222 at the target implant site, sheet-like implant 250 may be deployed from implant delivery system 100. For instance, the physician may disengage distal movement lock 180 from implant delivery system 100 and advance implant delivery shaft 103 distally until implant spreader assembly 107 is uncovered from sheath member 101 and cap 105. Once implant spreader assembly 107 is uncovered, implant spreaders 151 may expand or unfold sheet-like implant within should 222.

Sheet-like implant 250 may then be affixed to the tendon while it is held against the tendon by implant delivery system 100. Various attachment elements may be used to fix the implant to the tendon. Examples of attachment elements that may be suitable in some applications include sutures, tissue anchors, bone anchors, and staples. Various attachment elements may be used to fix sheet-like implant 250 to the target implant site. Examples of attachment elements that may be suitable in some applications include sutures, tissue anchors, bone anchors, and staples. Details of exemplary tendon staples may be found in commonly assigned co-pending applications: U.S. application Ser. No. 12/684,774 filed Jan. 8, 2010; U.S. application Ser. No. 12/729,029 filed Mar. 22, 2010; U.S. application Ser. No. 12/794,540 filed Jun. 4, 2010; U.S. application Ser. No. 12/794,551 filed on Jun. 4, 2010; U.S. application Ser. No. 12/794,677 filed on Jun. 4, 2010; and U.S. Application No. 61/443,180 filed on Feb. 15, 2011, the disclosures of which are incorporated herein by reference. Exemplary bone staples are described in commonly assigned applications: U.S. Application No. 61/577,626 filed Dec. 19, 2011; U.S. Application No. 61/577,632 filed Dec. 19, 2011 and U.S. Application No. 61/577,635 filed Dec. 19, 2011, the disclosures of which are incorporated herein by reference. Exemplary staples in many of the above applications may be used for anchoring in both soft tissue and in bone.

In the exemplary embodiment of FIG. 15B, the shaft of a fixation tool 210 is shown extending into shoulder 222. In one exemplary embodiment, fixation tool 210 is capable of affixing the implant to the tendon and bone with one or more staples while the implant may be held against the tendon by implant delivery system 100.

Figure 16A:
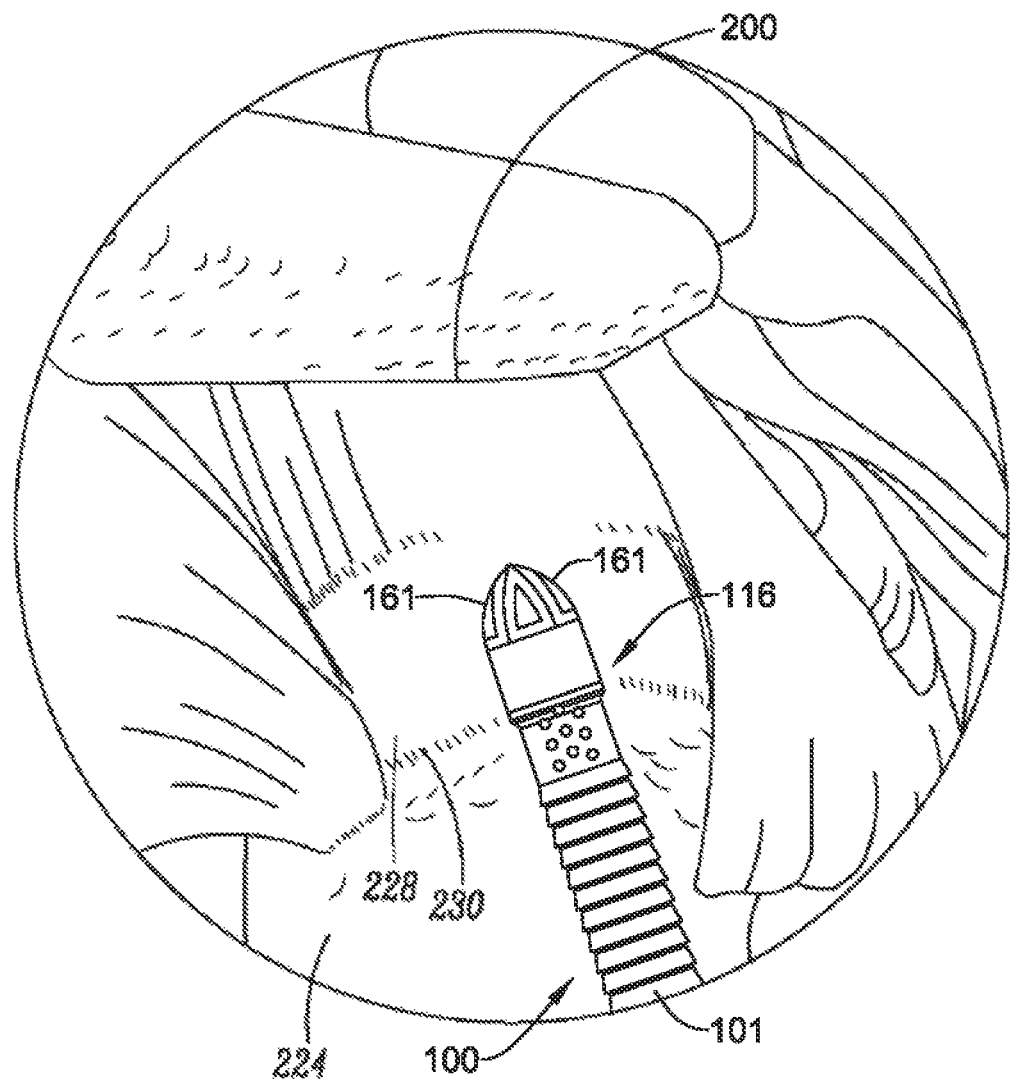
FIG. 16A is a partial view of a shoulder including an exemplary implant delivery device, according to an example of the present disclosure.
Figure 16B:
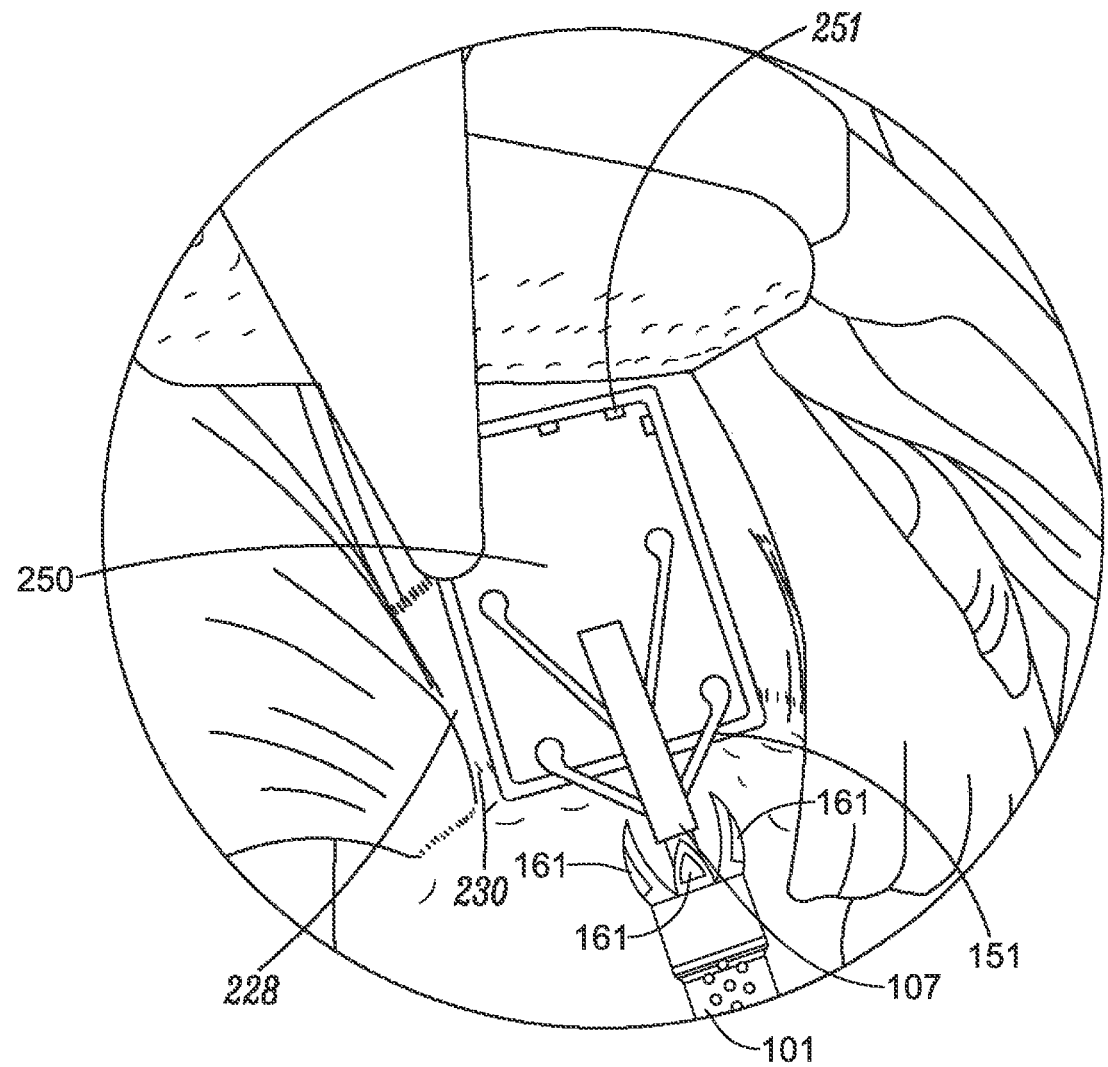
FIG. 16B is a partial view of a shoulder including a deployed sheet-like implant, according to an example of the present disclosure.

FIGS. 16A and 16B depict deployment of sheet-like implant 250 internally to shoulder 222. In these illustrations, the supraspinatus tendon is used as an example only. Implant delivery system 100 may be used to deliver implants to other areas of the body.

A view of the bursal side of supraspinatus tendon 228 is illustrated in FIG. 16A. Although drawn with a clear visible line at the frontal margin of the supraspinatus tendon, due to other tissue and ligaments in the area, this may generally not be visible to the surgeon through the arthroscope. Accordingly, in some examples, a physician may place markers (not shown) while viewing the biceps tendon from the articular side to delineate the front edge of where one would want to place the implant.

Generally, implant delivery system 100 may be used without the aid of a guidewire. Accordingly, the physician may begin by simply inserting the distal end of implant delivery system 100 into shoulder 222 through an incision or cannula and maneuvering the distal end to target implant site 200, as shown in FIG. 16A.

Once the distal end of implant delivery system 100 is positioned at target implant site 200, the physician may advance implant delivery shaft 103 distally. If implant delivery system 100 includes an engaged distal movement lock, such as distal movement lock 170, the physician may need to first disengage the distal movement lock. As the physician advances implant delivery shaft 103 distally, implant spreader assembly 107 attached to the distal end of implant delivery shaft 103 may begin to push on the inside of petals 161. This force may cause petals 161 to expand outward, creating an opening to lumen 117 of sheath member 101, or widening an existing opening, such as narrow opening 167 described with respect to FIGS. 5 and 6. Once implant spreader assembly 107 has been advanced distally beyond petals 161, implant spreader assembly 107 may be completely uncovered by sheath member 101 and petals 161.

When sheet-like implant is loaded onto implant spreader assembly 107, sheet-like implant 250 may be wrapped, folded, or rolled around implant spreaders 151. Once implant spreaders 151 are uncovered, implant spreaders 151 may then expand from their compact configuration to their expanded configuration. Accordingly, this expanding motion may thereby impart a force on sheet-like implant 250, causing sheet-like implant 250 to expand or unfold into a generally planar configuration. FIG. 16B depicts where implant spreader assembly 107 has been advanced distally beyond petals 161 and implant spreaders 151 have expanded sheet-like implant 250.

Once sheet-like implant 250 has been deployed at the target implant site, sheet-like implant 250 can be attached in multiple locations to supraspinatus tendon 228 using staples 251 or other fasteners, also shown in FIG. 16B. In at least some embodiments, spreaders 151 may be used to help hold sheet-like implant against supraspinatus tendon 228 while staples 251 are deployed to secure sheet-like implant 250 to supraspinatus tendon 228. Once the medial edge is attached, implant delivery system 100 may then be removed from the target implant site.

It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed:

1. An implant delivery system comprising:
a sheath member having a lumen therein;
an implant delivery shaft having a distal end region disposed within the sheath member such that the implant delivery shaft is longitudinally moveable relative to the sheath member;
an implant spreader assembly attached to the distal end region of the implant delivery shaft,
a sheet-like implant attached to the implant spreader assembly; and
a plurality of petals arranged around a distal end of the sheath member, each petal extending from a first end coupled to the distal end of the sheath member to a second free end defining a tip;
wherein the implant delivery shaft is longitudinally moveable relative to the sheath member to advance the implant spreader assembly and the sheet-like implant attached thereto out of the lumen of the sheath member;
wherein each of the plurality of petals is radially deflectable in a radially outward direction from a first closed configuration to a second expanded configuration as the implant spreader assembly and the sheet-like implant are passed out of the lumen distal of the plurality of petals;
wherein each petal is separated from adjacent petals by a gap extending from the first end to the second end and the gap between petals is narrower at the first end of adjacent petals than at the second end when the plurality of petals is in the first closed configuration.

2. The implant delivery system of claim 1, wherein the plurality of petals comprises an even number of petals.

3. The implant delivery system of claim 1, wherein each of the plurality of petals is disposed opposite another of the plurality of petals.

4. The implant delivery system of claim 1, wherein the plurality of petals are configured to collapse together when inserted into tissue.

5. The implant delivery system of claim 4, wherein, when collapsed together, the plurality of petals form a plug and prevent tissue from entering the lumen of the sheath member as the implant delivery system is advanced into the tissue.

6. The implant delivery assembly of claim 1, wherein the plurality of petals are biased toward a central longitudinal axis of the implant delivery shaft in the first configuration and are deflected radially outward in the second configuration.

7. The implant delivery system of claim 6, wherein the plurality of petals define an opening at a distal end thereof when the plurality of petals are in the first configuration.

8. The implant delivery system of claim 7, wherein each of the plurality of petals curves inward toward the central longitudinal axis in a distal direction.

9. The implant delivery system of claim 8, wherein each of the plurality of petals tapers in the distal direction.

10. The implant delivery system of claim 1, wherein the implant spreader assembly includes four separate arms, wherein the four arms are elastically deformed to be retained within the lumen.

11. The implant delivery system of claim 1, wherein the sheath member includes a plurality of holes extending through a sidewall thereof.

12. An implant delivery system comprising:
a sheath member having a lumen therein;
an implant delivery shaft having a distal end region disposed within the sheath member such that the implant delivery shaft is longitudinally moveable relative to the sheath member;
an implant spreader assembly attached to the distal end region of the implant delivery shaft and including four separate arms elastically deformed such that each arm is configured to automatically expand from a compact configuration within the lumen of the sheath member to a radially expanded configuration outside the sheath member;
a sheet-like implant attached to the implant spreader assembly; and
a plurality of petals arranged around a distal end of the sheath member;
wherein the implant delivery shaft is longitudinally moveable relative to the sheath member to advance the implant spreader assembly and the sheet-like implant attached thereto out of the lumen of the sheath member;
wherein each of the plurality of petals is radially deflectable in a radially outward direction from a first configuration to a second expanded configuration as the implant spreader assembly and the sheet-like implant are passed out of the lumen distal of the plurality of petals;
wherein first and second arms of the four arms extend in a first direction from a first longitudinal position on the implant spreader and the third and fourth arms of the four arms extend in the first direction from a second longitudinal position on the implant spreader, wherein the first and second longitudinal positions are longitudinally spaced apart from one another.

* * * * *